US010020176B2

(12) United States Patent
Rorick et al.

(10) Patent No.: US 10,020,176 B2
(45) Date of Patent: Jul. 10, 2018

(54) SURFACE EXTRACTION INTERFACE

(71) Applicant: Advion Inc., Ithaca, NY (US)

(72) Inventors: Cody Scott Rorick, Van Etten, NY (US); Nathan Corwin, Ithaca, NY (US); Jamey Jones, Ithaca, NY (US)

(73) Assignee: Advion Inc., Ithaca, NY (US)

( * ) Notice: Subject to any disclaimer, the term of this patent is extended or adjusted under 35 U.S.C. 154(b) by 62 days.

(21) Appl. No.: 14/993,662

(22) Filed: Jan. 12, 2016

(65) Prior Publication Data

US 2016/0203965 A1 Jul. 14, 2016

Related U.S. Application Data

(60) Provisional application No. 62/102,321, filed on Jan. 12, 2015.

(51) Int. Cl.
*H01J 49/00* (2006.01)
*H01J 49/04* (2006.01)
*G01N 30/95* (2006.01)
*G01N 30/72* (2006.01)

(52) U.S. Cl.
CPC .......... *H01J 49/0431* (2013.01); *G01N 30/95* (2013.01); *G01N 30/7233* (2013.01)

(58) Field of Classification Search
CPC .. H01J 49/0431; G01N 30/95; G01N 30/7233
USPC ........................................ 250/281, 282, 288
See application file for complete search history.

(56) References Cited

U.S. PATENT DOCUMENTS

| 5,660,727 | A | * | 8/1997 | Gleave | ............... | B01D 11/0203 |
| | | | | | | 210/141 |
| 5,750,029 | A | * | 5/1998 | Houck | ............... | B01D 11/0203 |
| | | | | | | 210/137 |
| 2003/0020011 | A1 | | 1/2003 | Anderson et al. | | |
| 2011/0269166 | A1 | | 11/2011 | Van Berkel et al. | | |
| 2014/0248714 | A1 | * | 9/2014 | Shoemaker | ......... | B01L 3/50255 |
| | | | | | | 436/501 |

OTHER PUBLICATIONS

Notification of Transmittal of the International Search Report and the Written Opinion of the International Searching Authority, or the Declaration, International Application No. PCT/US2016/013012, dated Mar. 16, 2016, 12 pages.

* cited by examiner

*Primary Examiner* — Michael Maskell
(74) *Attorney, Agent, or Firm* — Fish & Richardson P.C.

(57) ABSTRACT

Surface extraction interface systems can include a seal assembly with a cavity assembly, an actuator, and a force gauge. Methods of preparing a sample for analysis can include: receiving data identifying characteristics of a surface supporting the sample; determining a pressure to be applied by a seal assembly against the surface; pressing a cavity assembly against the surface facing the open side of the cavity until the pressure is achieved; and extracting a sample from the surface by flowing a stream of extraction solvent through the sealed extraction cavity.

32 Claims, 26 Drawing Sheets

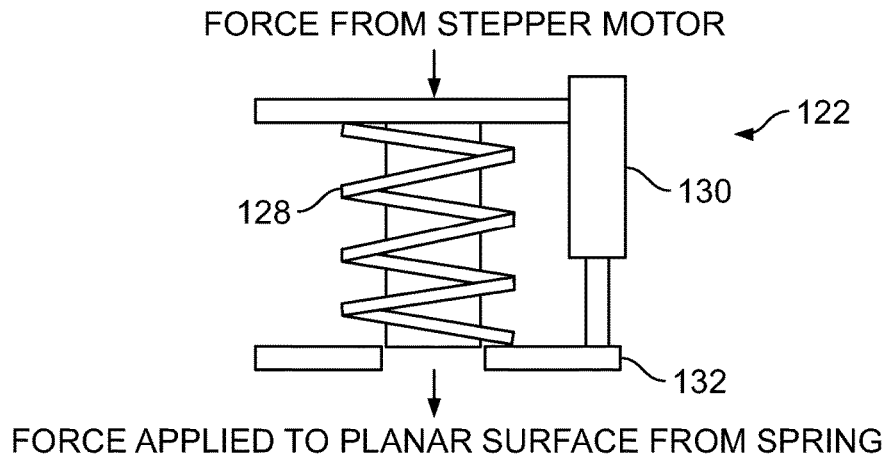
FIG. 3
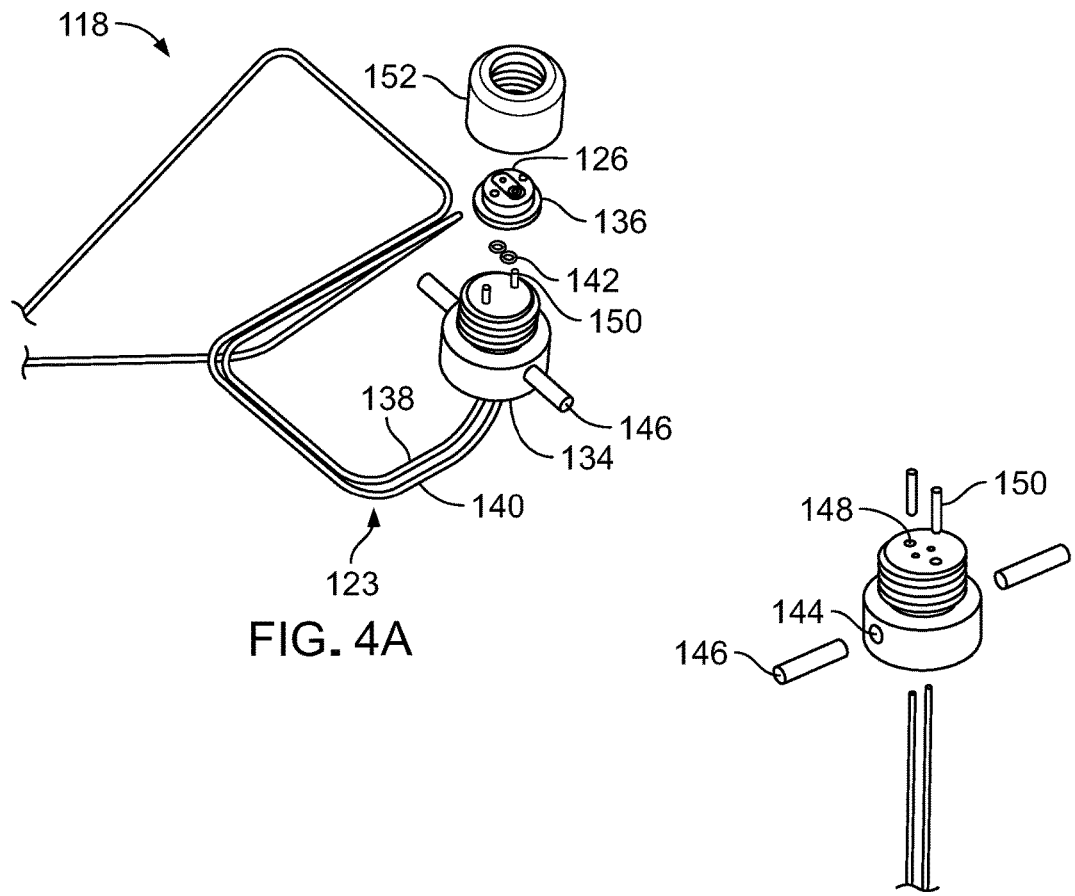
FIG. 4A
FIG. 4B

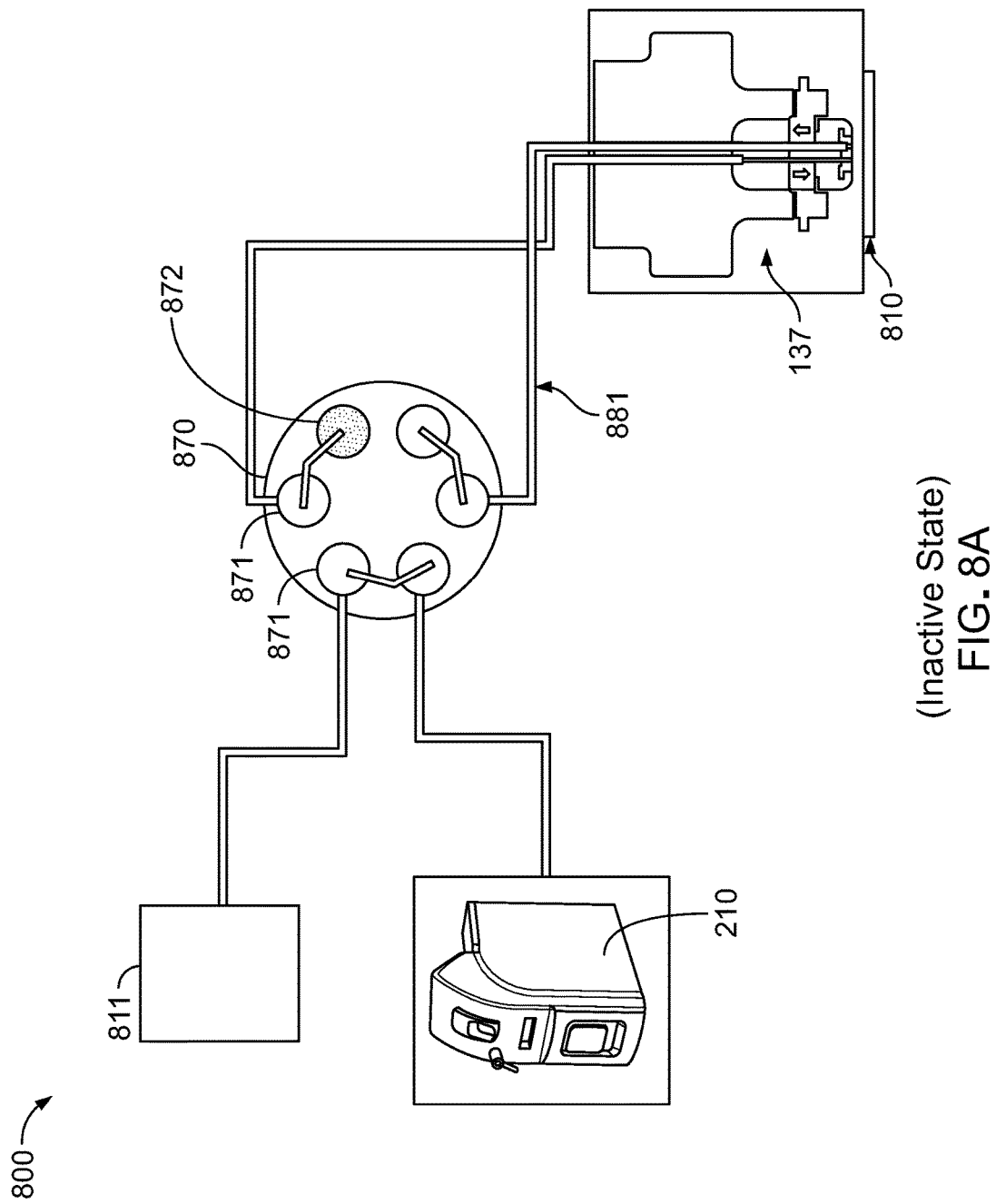
FIG. 8A (Inactive State)

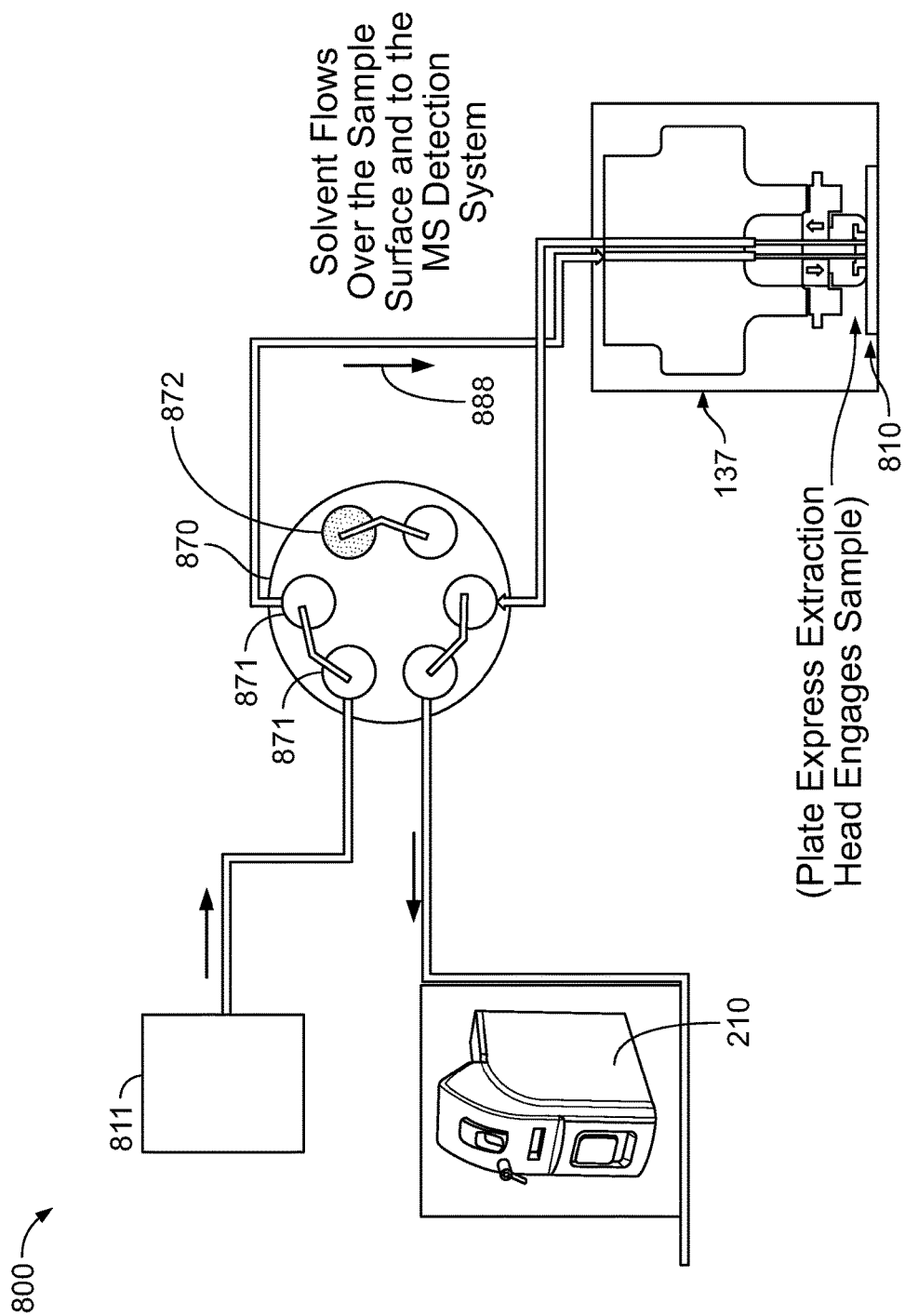

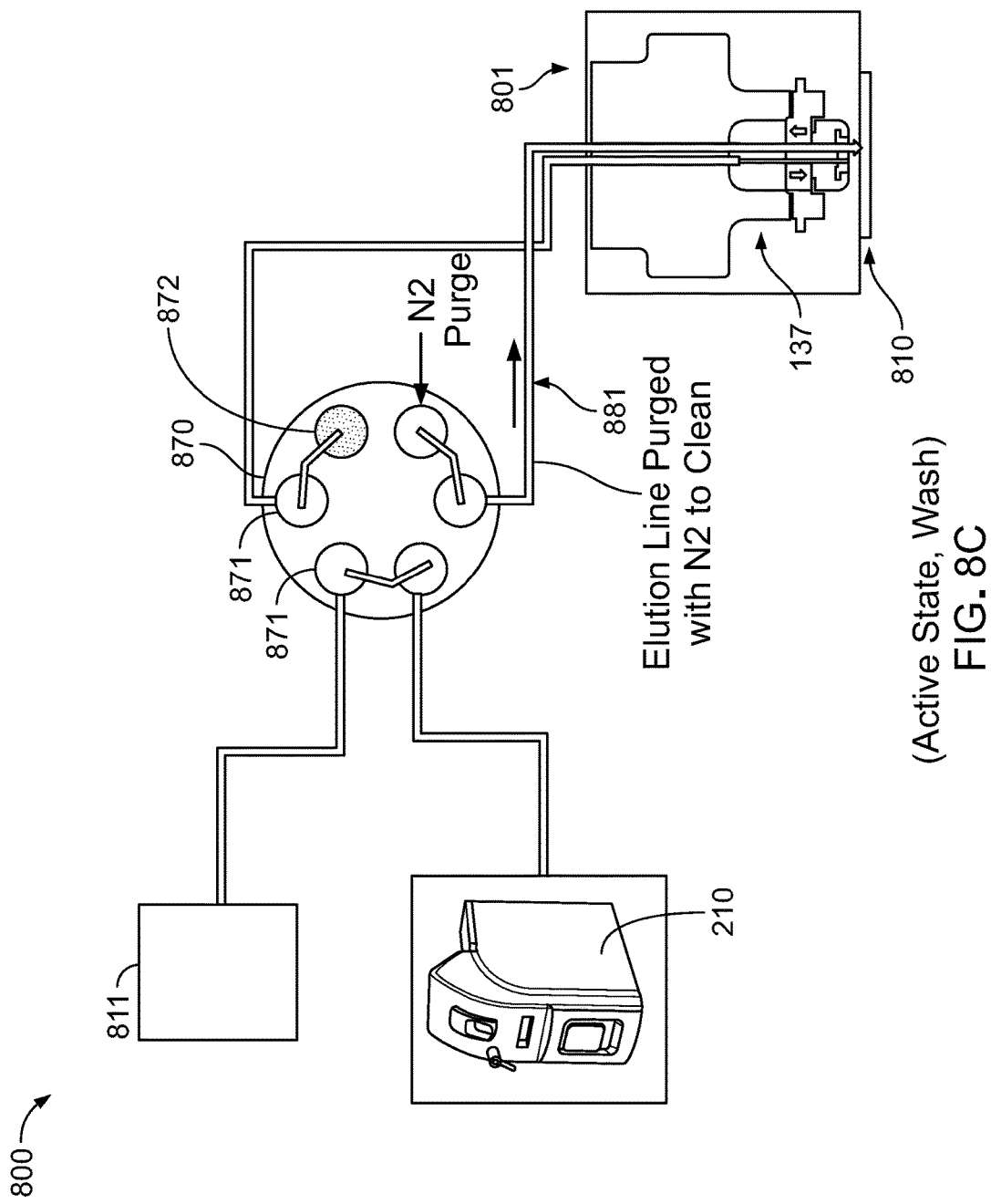

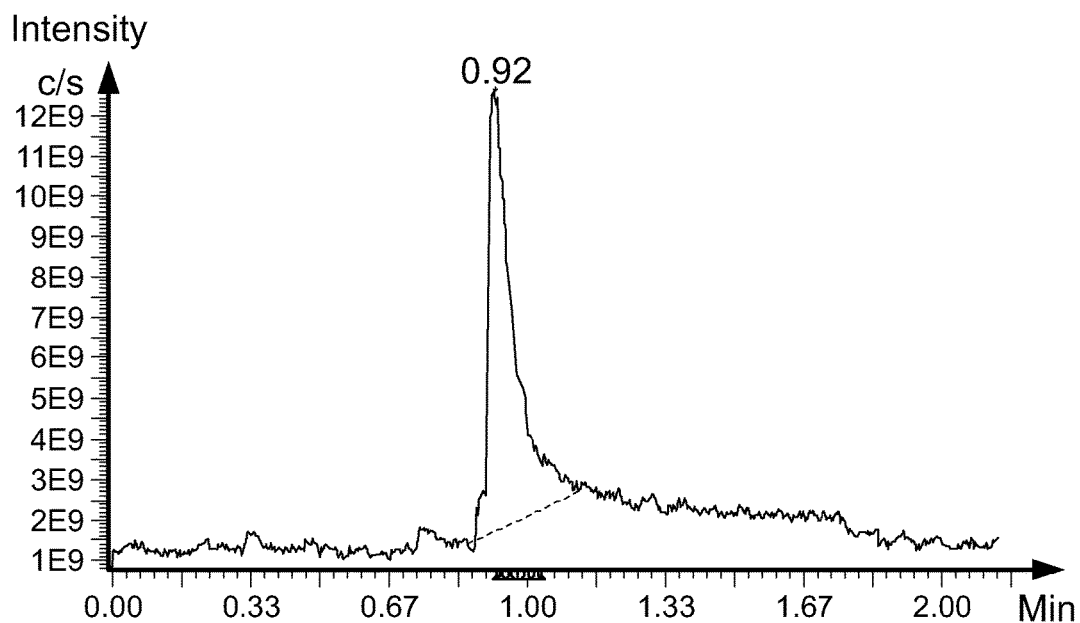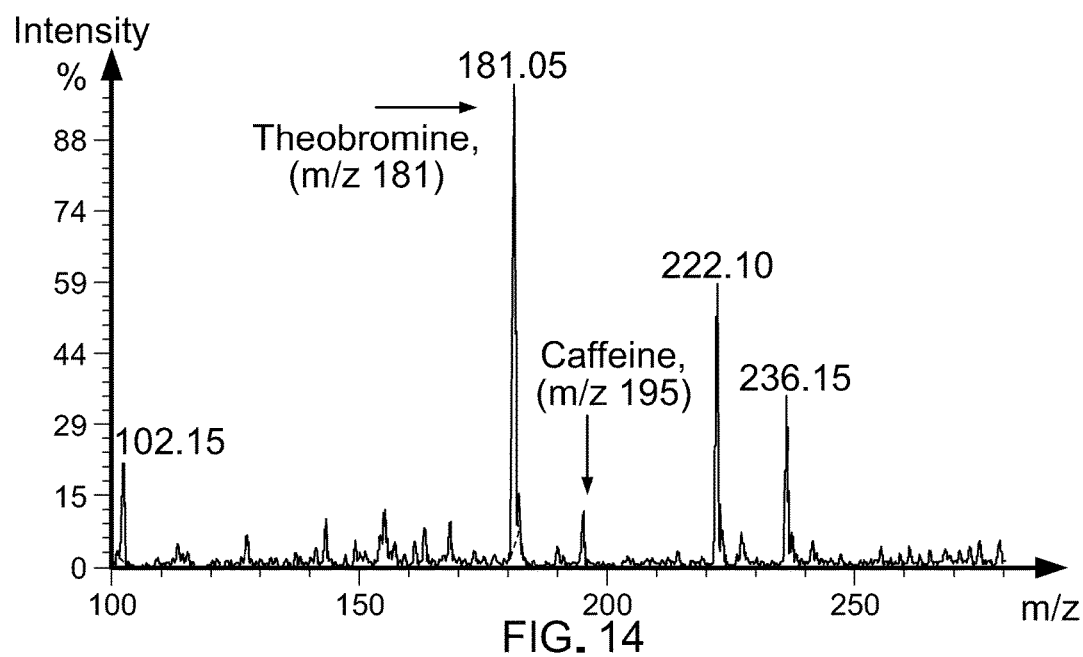
FIG. 14

SURFACE EXTRACTION INTERFACE

CLAIM OF PRIORITY

This application claims priority under 35 USC § 119(e) to U.S. patent application Ser. No. 62/102,321, filed on Jan. 12, 2015, the entire contents of which are hereby incorporated by reference.

FIELD

This disclosure relates to sample analysis from surfaces via liquid extraction and interface to mass spectrometry.

BACKGROUND

Direct surface sampling is a simple, cost-effective, and easy-to-operate technique that is used to analyze chemical and biochemical compounds from a variety of surface types such as paper, thin layer chromatography plates, tissue sections, plant material, technical surfaces such as polymers, or metals. Physical, chemical and/or optical methods can be used to locate, visualize detect and quantitate analytes on technical and biological surfaces. More recently, interfaces have been developed that allow such surfaces to be sampled with mass spectrometry by means of a liquid extraction on the surface and subsequent ionization in the source of the MS, which can be with or without liquid chromatography separation.

SUMMARY

This disclosure describes a versatile surface extraction-mass spectrometer interface systems and methods. These systems and methods include a seal assembly that controllably applies the appropriate force to seal a cavity of the interface against varying surfaces. Sealing the cavity against the surface or solid partially or completely limits the flow of fluids out of the cavity between the surface or solid and the structure of the interface defining the cavity. Some systems include a spring and potentiometer (e.g., a basic force gauge) combined with a stepper motor to apply contact pressure to seal liquids in a cavity above a surface.

These systems and methods can determine the appropriate pressure required based on a database of surfaces and required pressures. This enables the analysis of materials layered on surfaces where the materials have different surface characteristics and require varying pressures to seal the layered materials between the surface and cavity without leakage. For example, materials such as tissue cultures, dried blood spots, TLC plates, fruit skins, and biological or technical surfaces can support an analyte (e.g., on or in the surface) that can be extracted by liquid extraction for subsequent analysis.

In some systems, the cavity of the interface is defined by a modular cavity assembly with an inlet and an outlet. Each cavity assembly include walls that define the lateral extent of the cavity. The walls can be defined, for example, by protrusions that extend outward from a primary surface of the cavity.

Multi-piece cavity assemblies (e.g., with 3-piece bases) allow operators to switch out bases to use a base appropriate to specific sample. Different bases can have different sizes and shapes of cavities. Different bases can also have protrusions of different heights (e.g., 50-1000 microns) and made from different materials (knife edge from or round edge from, for example, a PTFE seal.

Some thin layer chromatography interface systems include: a seal assembly including: a cavity assembly defining a cavity with an inlet, an outlet, and an open side; an actuator operable to press the cavity assembly against an opposed surface facing the open side of the cavity; and a force gauge operable to measure a force applied by the seal assembly against the opposed surface. As used herein, "actuator" includes mechanical devices for moving or controlling something. For example, actuators include motors (e.g., electric stepper motors), pneumatic air cylinders, and pistons.

Some sample analysis systems include: the coupling of a mass spectrometer with an inlet port and a thin layer chromatography interface system with an outlet port and a seal assembly. The seal assembly includes: a cavity assembly defining a cavity with an inlet, an outlet, and an open side; a motor with an extendable shaft, the motor operable to press the cavity assembly against an opposed surface facing the open side of the cavity; and a force gauge operable to measure a force applied by the seal assembly against the opposed surface, wherein the force gauge comprises a spring and a potentiometer attached to the motor with the cavity assembly on one end of the motor shaft such that the force applied by the seal assembly against the opposed surface causes the spring to compress; and a channel connecting the output port of the thin layer chromatography interface system with the inlet port of the mass spectrometer. The assembly may also include a liquid chromatography column, or sample loop and a liquid chromatography column. The liquid chromatography column can separate the extracted analytes by time and will allow higher sensitivity detection of analytes due to separation of analytes from each other and from background matrix, e.g proteins extracted from dried blood spot cards. Adding a storage loop and switching method to the system allows to operate the chromatographic column independent from the cavity seal formed on the surface and enables high pressure chromatographic separation such as in UHPLC for faster analysis and higher separation capacity.

Embodiments of these systems can include one or more of the features described below.

In some embodiments, the actuator includes a motor with an extendable shaft. In some cases, the motor includes a stepper motor. In some cases, the force gauge includes a spring and a sensor attached to the motor with the cavity assembly on one end of the motor shaft such that the force applied by the seal assembly against the opposed surface causes the spring to compress. For example, the sensor can be a potentiometer.

In some embodiments, the cavity assembly includes an inlet/outlet assembly defining at least portions of the inlet and the outlet and a base detachably attached to the inlet/outlet assembly. In some cases, the cavity assembly includes a locking collar, the base detachably attached to the inlet/outlet assembly by the locking collar. In some cases, systems include a plurality of bases defining cavities with different configurations. In some cases, the cavity seal includes a metal knife edge or a PTFE seal ring, for example a Viton® seal ring.

In some embodiments, the seal assembly comprising a mechanical self-aligning washer.

In some embodiments, the outlet of the cavity includes a filter assembly. In some cases, the filter assembly includes a flush mounted filter or an inline filter.

In some embodiments, systems include a control system connected to the actuator and the force gauge, the control system responsive to input data identifying characteristics of the opposed surface to determine a force to be applied by the seal assembly against the opposed surface and to operate the actuator to achieve the desired force.

In some embodiments, systems include plumbing enabling backflushing of a sample line with nitrogen gas for cleaning purposes.

Some methods of preparing a sample for analysis include: receiving, by a control system connected to an actuator and a force gauge, identifying characteristics of a surface supporting the sample; determining a pressure to be applied by a seal assembly against the surface; sending a control signal from the control system to the actuator to operate the actuator to press a cavity assembly defining a cavity with an inlet, an outlet, and an open side against the surface facing the open side of the cavity until the pressure is achieved; and extracting a sample from the surface. Embodiments of these methods can include one or more of the features described below.

In some embodiments, the force gauge includes a spring and a sensor attached to the motor such that pressing the cavity assembly against the surface causes the spring to compress.

In some embodiments, methods include assembling the cavity assembly by detachably mounting a base on an inlet/outlet assembly. In some cases, methods include selecting the base from a plurality of bases In some embodiments, methods include selecting one base from a plurality of bases defining cavities with different configurations. In some cases, methods include forming the cavity assembly by detachably mounting the selected base on an inlet/outlet assembly defining at least portions of the inlet and the outlet. In some cases, determining the pressure comprises accessing a database of surfaces and associated pressures.

The described systems and methods can be used to achieve the high sensitivity, high specificity and high throughput analysis of samples containing analytes of interest provided by mass spectrometry while simplifying the sample preparation required before mass spectrometer analysis can begin. These systems and methods can reduce the issues such as selecting the column (size and material), gradient profiles, run times, dilution ratios, sample concentrations, etc., that often make liquid chromatography challenging and costly. These systems and methods can also significantly reduce the run times (e.g., ranging from ~10 minutes to more than 60 minutes) associated with other liquid chromatography methods, thus reducing the associated costs and waste disposal issues.

The systems and methods described in this disclosure often require only a few minutes for sample extraction and analysis. For example, the development of a TLC plate identifies sample spots and extraction of the sample to the mass spectrometer typically takes less than one minute while consuming less than 1 ml of solvent. Because of its low volume characteristics, these systems and methods can dramatically reduce solvent consumption as well as run times, method development and human resource requirements.

Other surfaces of interest can entail whole body sections of small rodents (rats, mice) in PK/PD studies of small molecule drugs. Advantages could include the rapid localization of drugs and metabolites, rapid determination of metabolites forming in vivo and in specific location, drug distribution throughout the analyzed species and semi-quantitative comparison between tissues, organs and different drugs These systems and methods can also be used for analysis of fruit, vegetable or other edibles for chemical residues such as pesticides on the outer surface or inner sections.

These systems and methods can also be used for analysis of dried blood spots (DBS) for the rapid sample throughput in PK/PD studies in blood (human or animal) in sample limited circumstances (rodent animal models), circumstances with limited ability to draw blood samples (children) or sampling circumstances that prevent freezing of blood samples (third world countries). DBS surfaces provide a dried blood samples that is inactive with regards to pathogens and hence can be handled easier and more safely than blood samples. Also DBS cards and specialized surfaces can provide significant sample clean up, pre concentration or matrix removal prior to a surface extraction—MS combined analysis.

These systems and methods can also be used for analysis of e-waste plastic particles via surface extraction/MS to detect types of plastics and/or potential contaminations and/or to determine the value of the respective e-waste prior to further processing.

These systems and methods can also be used for analysis of swabs enabling indirect surface analysis of swabbed locations.

These systems and methods can also be used for analysis of paper having a finger print thereon.

The details of one or more embodiments of these systems and methods are set forth in the accompanying drawings and the description below. Other features, objects, and advantages will be apparent from the description and drawings, and from the claims.

DESCRIPTION OF DRAWINGS

FIG. 3 is a schematic of a force gauge.

FIGS. 4A and 4B are perspective views of a cavity assembly in a more detailed view of an inlet/outlet assembly of the cavity assembly, respectively.

FIGS. 8A-C are diagrams of the operation of a surface extraction interface system with a nitrogen purging system.

FIG. 14 is a graph of mass spectrometry data of a surface sample extracted from a test swab.

Like reference symbols in the various drawings indicate like elements.

DETAILED DESCRIPTION

Versatile surface extraction interface systems and methods include a seal assembly that controllably applies the appropriate force to seal a cavity of the interface against varying surfaces and solids. Planar surfaces are preferred for ease manipulation and evenness of surface but non-planar surfaces can be accommodated by 'manual' base/probe that are held against the surface of an apple, tooth, or other non-planar surface being samples.

Sealing the cavity against the surface or solid partially or completely limits the flow of fluids out of the cavity between the surface or solid and the structure of the interface defining the cavity. Aided by determining the appropriate pressure required based on a database of surfaces and required pressures, these systems and methods can be used in the analysis of materials layered on surfaces (e.g., planar surfaces) where the materials have different surface characteristics and require varying pressures to seal the layered materials between the surface and cavity without leaking. For example, materials such as tissue sections, dried blood spots, TLC plates, fruit skins, and biological or technical surfaces can support an analyte (e.g., on or in the surface) that can be extracted by liquid extraction for further analysis.

Figure 1:
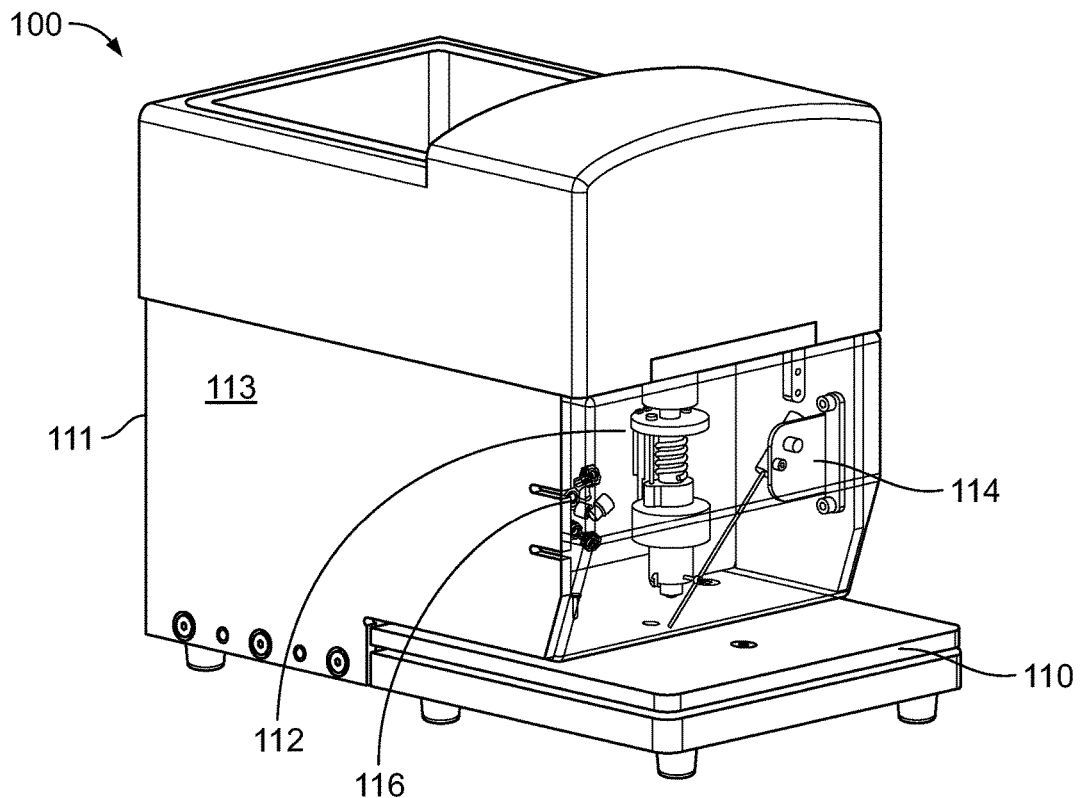
FIG. 1 is a perspective view of a surface extraction interface system.

FIG. 1 shows an example surface extraction interface system 100 that includes a platform 110 on which sample bearing surfaces (e.g., TLC plates, tissue sections, and fruit skins) are placed for extraction. A housing 111 contains a control system 113 and supports and protects other components of the surface extraction interface system 100. A seal assembly 112 is operable to seal a cavity of the interface against a surface from which the sample is being extracted. A guide 114 designates the spot under the seal assembly 112 where the cavity of the interface will be placed when the lower end of the seal assembly 112 is lowered to contact the sample bearing surface. The surface extraction interface system 100 uses a laser as the guide 114 but some surface extraction interface systems use other means of designating the spot under the seal assembly 112. A fluid valve assembly (e.g., a 6 port valve assembly) 116 is used to route a stream of extraction liquid from an LC system or LC pump into the mass spectrometer ionization source by either bypassing the surface extraction system sending the extraction thru the head assembly and then into the mass spectrometer.

Figure 2:
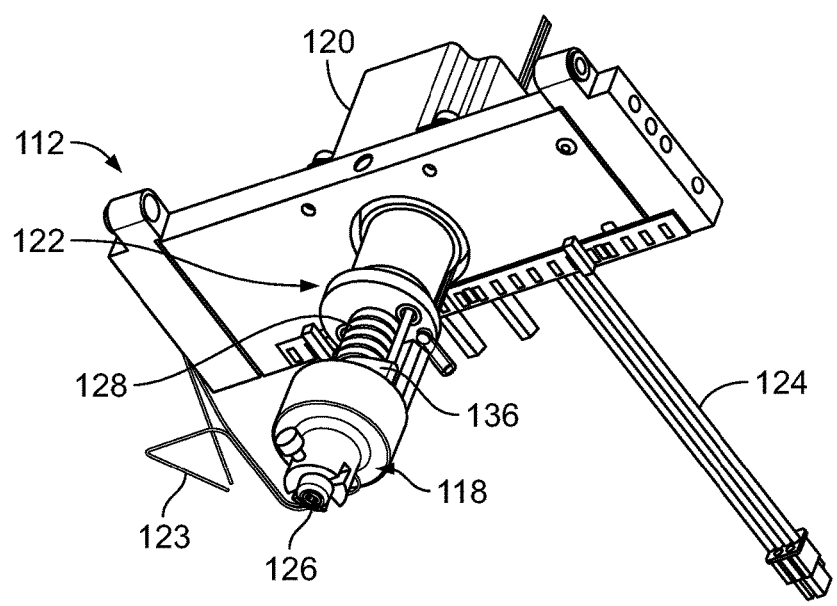
FIG. 2 is a perspective view of a seal assembly for a surface extraction-mass spectrometer interface system.

FIG. 2 shows the seal assembly 112 used in the surface extraction interface system 100. The seal assembly 112 includes a cavity assembly 118 (shown in more detail in FIG. 4A), an actuator 120, and a force gauge 122 (shown in more detail in FIG. 3). Solvent lines 123 (also shown in FIG. 4A) carry extraction solvent to and extracted sample away from the seal assembly 112. Input/output lines 124 carry electricity and control/sensor signals to the seal assembly 112 and carry control/sensor signals away from the seal assembly 112.

The cavity assembly 118 defines a cavity 126 (shown in more detail in FIGS. 5 and 6) with an open side. The actuator 120 is operable to press the cavity assembly 118 against an opposed surface facing the open side of the cavity 126. This motion causes the seal assembly 112 to apply pressure against the opposed surface (e.g., the sample-bearing surface). The actuator 120 of seal assembly 112 is a linear, bipolar stepper motor with 0.0211 mm full-step resolution and a 500 Newtons of force capability. The cavity assembly 118 is mounted on a shaft extending from the stepper motor.

A stepper motor provides precise positioning, excellent repeatability, excellent response to starting and stopping and long life. Some seal assemblies use other mechanical devices for moving the cavity assembly 118 towards or away from a sample-bearing surface. For example, some seal assemblies use air cylinders, air pistons, or simple springs with rewinding motors as actuators but they have lower resolution of control and are less repeatable.

FIG. 3 is a schematic showing an example force gauge 122 that is operable to measure the pressure applied by the seal assembly 112 against the opposed surface in response to the action of the actuator 120. The force gauge 122 includes a spring 128 and a sensor 130 (e.g., a potentiometer). When the actuator 120 presses the cavity assembly 118 against a surface, the spring is compressed against a surface 132 that is fixed in position relative to the cavity assembly. For example, the surface 132 can be the upper end of the cavity assembly as illustrated in FIG. 2. The surface extraction interface system 100 calculates the pressure being applied to the sample-bearing surface using Hooke's Law for spring force based on characteristics of the spring 128 and the amount of compression of the spring 128. In surface extraction interface system 100, signals indicating the degree of spring compression are sent over input/output lines 124 (FIG. 2) to the control system 113 (FIG. 1). In some interface systems, the force calculations are performed locally on the force gauge and the calculated forces/pressures are sent to the control system 113. The example system has ~1 Newton resolution pressure control but it is anticipated that pressure control resolution of up to about 5 Newtons will be effective.

The control system 113 is connected to the actuator 120 and the force gauge 122. The control system is responsive to input data identifying characteristics of the opposed surface to determine a force to be applied by the seal assembly 112 against the opposed surface and to operate the actuator 120 to achieve the force. For example, the control system 113 can include a program with a stored list (e.g., in a database) of surface pressures associated with different surfaces. In response to user input indicating the type of surface, the control system 113 determines and, through the actuator 120, applies the appropriate pressure. This approach enables different surface conditions and surface porosities to be sealed with pressures ranging from a few pounds of pressure up to 200 pounds of applied pressure. In some systems, users input surface characteristics (e.g., surface roughness, surface porosity, media bed thickness) rather than or in addition to inputting the type of surface. In some systems, the control system is connected to sensors which measure characteristics of the sample bearing surface which are used as input to determine the appropriate sealing pressure.

FIGS. 4A and 4B illustrate an example cavity assembly 118. The cavity assembly 118 includes an inlet/outlet assembly 134 supporting a base 136 (shown in FIG. 4A and, in more detail in FIG. 5). The base 136 is detachably attached to the inlet/outlet assembly so that different bases can be used for different surfaces and/or analytes. The base 136 has walls that define the lateral extent of the cavity 126. In this case, the cavity 126 is an oval shaped cavity.

The surface extraction interface system 100 is provided with a plurality of bases defining cavities with different configurations. For example, this modular design allows for the use of cavity shapes ranging from circles 300 um in diameter to much larger circles and ovals. Oval extraction cavities with a size of approximately 4 by 2 mm are appropriate for use with medium performance thin layer chromatography surfaces that typically form 4 mm long lines of analytes after sample chromatography with varying line thickness depending on sample concentration. Round cavities of 1-4 mm of diameter can be used for surfaces such as plastic e-waste, edibles and dried blood spots. These surfaces usually do not require high spatial resolution of the surface extraction, but benefit from an increase in sample surface since this increase in area increases the absolute amount of extracted analyte, and hence, the sensitivity of the analysis. Round cavities of 300-1000 um can be employed for the analysis of tissue sections where the spatial information and distribution analysis of drugs or metabolites is of interest or high performance 2 dimensional TLC where analytes are usually concentrated in 1 mm spots.

The solvent lines 123 (also shown on FIG. 2) include a fluid inlet line 138 and a fluid outlet line 140 (shown in FIGS. 4A and 4B). The fluid inlet line 138 and the fluid outlet line 140 extend through the inlet/outlet assembly 134 into the base 136. Two O-rings 142 are disposed around the fluid inlet line 138 and the fluid outlet line 140 between the inlet/outlet assembly 134 and the base 136 to limit or prevent leakage around the fluid inlet line 138 and the fluid outlet line 140. The fluid inlet line 138 carries solvent to the cavity 126 defined by the base 136. The fluid outlet line 140 carries extracted sample material away from the cavity 126.

The inlet/outlet assembly 134 defines side bores 144 that receive alignment dowel pins 146 that maintain the alignment of the inlet/outlet assembly 134 relative to the cavity assembly 118. The inlet/outlet assembly 134 also defines end bores 148 that receive alignment dowel pins 150 that maintain the alignment of the base 136 relative to the inlet/outlet assembly 134. To assemble the cavity assembly 118, the alignment dowel pins 146, 150 are inserted into the inlet/outlet assembly 134. The fluid inlet line 138 and the fluid outlet line 140 are inserted through the inlet/outlet assembly 134 to be flush to 0.05 mm sub-flush to the inlet/outlet assembly 134. The O-rings 142 are placed over the ends of the fluid inlet line 138 and the fluid outlet line 140. After the base 136 is mounted onto the inlet/outlet assembly 134, a retaining collar 152 is placed over the base 136 to hold the base 136 in place. In the cavity assembly 118, the retaining collar 152 is screwed down onto threads defined in the outer surface of the inlet/outlet assembly 134. Some cavity assemblies use other retaining mechanisms such as, for example, latches.

The cavity assembly 118 includes a self-leveling feature that by design provides the cavity assembly 118 freedom of movement in all directions. Other cavity assemblies use other self-leveling mechanisms such as, for example, O-rings or Bellville washers. The self-aligning feature of the cavity assembly 118 provides even compression against the sample bearing surface. This even compression can reduce the likelihood of leakage out of the cavity 126 between the sample bearing surface and the cavity assembly.

Figure 5:
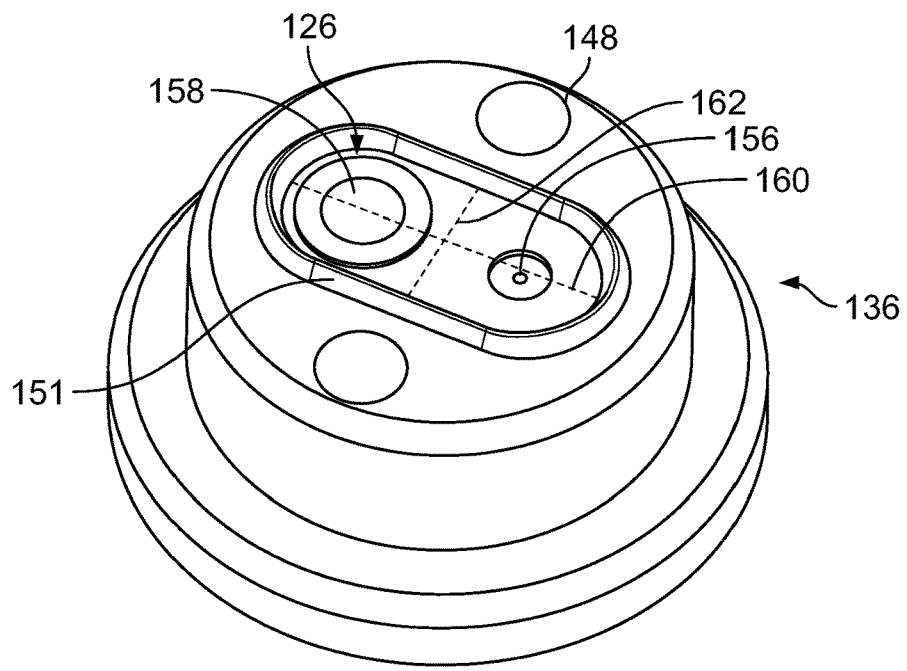
FIGS. 5 and 6 are perspective views of bases for use in a cavity assembly.
Figure 6:
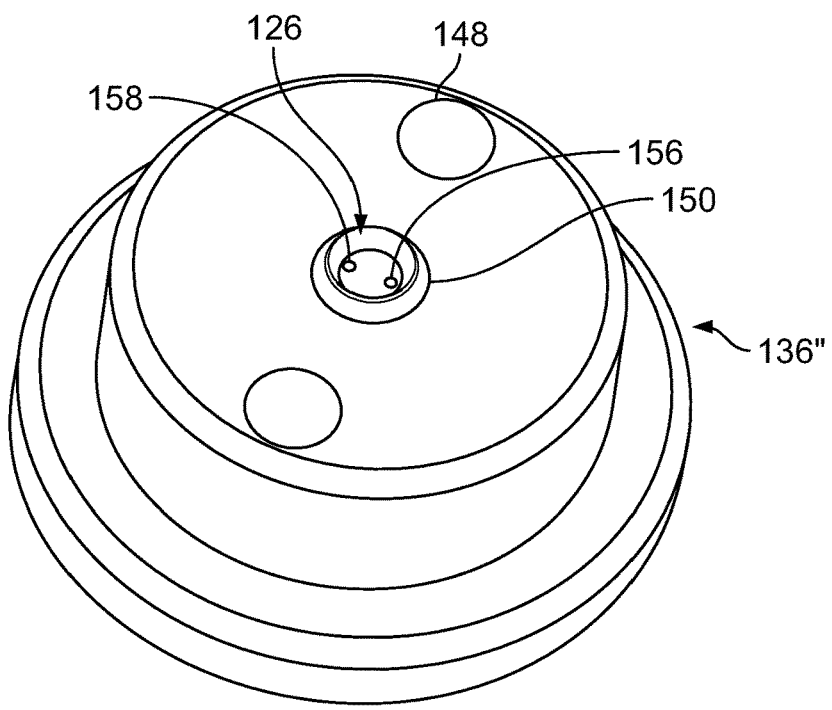

FIG. 5 shows the base 136 in more detail and FIG. 6 illustrates another base 136" usable with the cavity assembly 118 shown in FIGS. 2, 4A, and 4B. Each cavity assembly 118 includes walls that define the lateral extent of the cavity 126. The cavities 126 of these bases 136, 136" have walls defined by protrusions 151 that extend outward from a primary surface of the cavity 126. Walls formed by knife-edged protrusions are anticipated to form a good seal with the sample bearing surface. These bases 136, 136" have protrusions extending 250 microns outward from the primary surface of the cavity 126. Other bases have protrusions of different heights (e.g., 50-1000 microns) dependent on the surface requirements. The knife-edge protrusions may define a variety of different depths, for example, 500 um, 150 um, and 100 um, and the size of the rim may be, for example 2×4 mm down to 1 mm diameter.

Each cavity 126 has an inlet 156 and an outlet 158 that are in fluid communication with the fluid inlet line 138 and the fluid outlet line 140, respectively. Some bases include a filter assembly to reduce the likelihood that particulates in the extracted material clog downstream parts of the system. For example, the base 136 shown in FIG. 5 has a filter assembly that includes a flush mounted filter. Some cavity assemblies include other filters such as, for example, inline filters in fluid outlet line 140.

Multi-piece cavity assemblies (e.g., with an inlet/outlet assembly 134, a base 136, and a retaining collar 152) allow operators to switch out bases to use a base 136 appropriate to specific sample. Different bases can have different sizes and shapes of cavities. For example, the base 136 shown in FIG. 5 has oval shaped cavity 126 with a longitudinal axis 160 that is 4 mm long and a transverse axis 162 that is 2 mm long. For a wall height of 250 microns, this configuration provides a cavity with volume of approximately 16.6 mm$^3$. In another example, the base 136" shown in FIG. 6 has a circular shaped cavity with a diameter of 1 mm. For a wall height of 250 microns, this configuration provides a cavity with volume of approximately 1.83 mm$^3$. Oval cavities can have longitudinal axes ranging in length from 1 mm to 4 mm and transverse axes ranging in length from 1 mm to 2 mm. These cavities (e.g., 2×4 mm cavities) are good for analysis of low resolution TLC, edibles, plastic e-waste, and other applications that are not sensitive to spatial resolution. Circular cavities can have diameters ranging in length from 1 mm to 2 mm. Circular cavities with 1 mm diameter are good for high resolution TLC while circular cavities with 300 um diameter are good for tissue sections and spatial resolution sensitive applications. Cavities with defined sizes in general are very helpful in DBS analysis since they define the absolute amount of blood samples since blood distributes (saturates the card surface) and stretches out according to volume dropped on the card.

Figure 7:
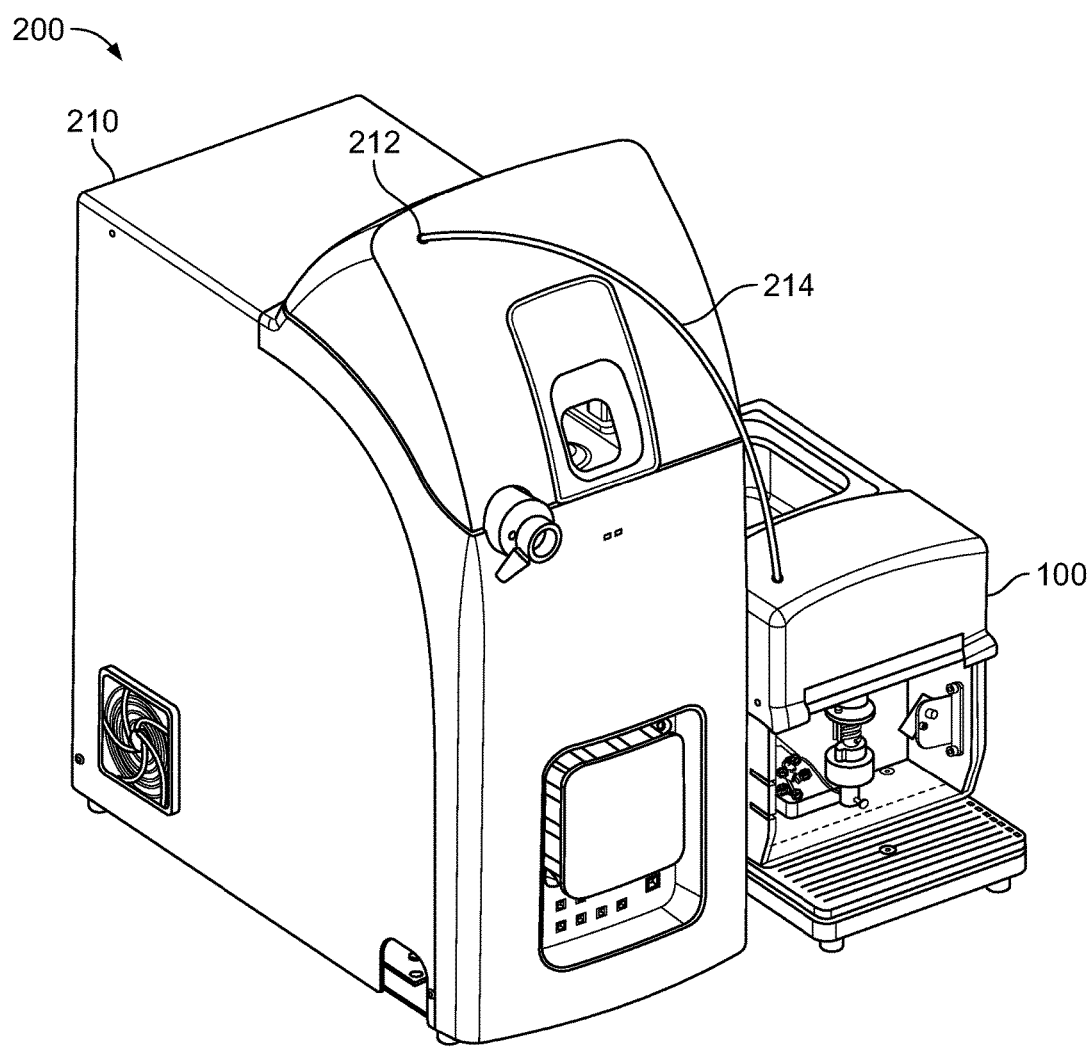
FIG. 7 is a perspective view of a sample analysis system with a mass spectrometer and a surface extraction interface system.

As shown in FIG. 7, a sample analysis systems 200 can include a mass spectrometer 210 with an inlet port 212 receiving analyte from the surface extraction interface system 100 through a channel 214 connecting the output port of the thin layer chromatography interface system with the inlet port of the mass spectrometer.

In operation, the surface extraction interface system 100 can be used to prepare samples for analysis by a mass spectrometer. We describe the operation as used to extract a sample from a typical edible such as grape skin, apple skin or peach skin for the detection of pesticide residues in MS but samples can be extracted from other sample bearing surfaces such as, for example, a TLC plate, a dried blood spot card or other modified medium or a thin whole body tissue section using similar operations. The system can also be used for other applications such as, for example, analyzing sheets of paper from a printer in an automated fashion for product control in paper industry.

In systems with multi-piece cavity assemblies, the user assembles the cavity assembly 118 by detachably mounting the base 136 on the inlet/outlet assembly 134. The user can select the base 136 from a plurality of bases with different cavity configurations based on the spatial requirement of the information obtained from the surface, e.g., the above described extraction cavity of 4 by 2 mm for low spatial resolution but maximum analyte sensitivity before detachably mounting the selected base 136 on the inlet/outlet assembly 134. The user then mounts the assembled cavity assembly 118 on the surface extraction interface system 100.

The user places the grape skin section on the platform 110 such that the portion of the grape skin surface from which the sample is being extracted is under the laser marker indicating the spot under the seal assembly 112 where the cavity of the interface will be placed when the lower end of the seal assembly 112 is lowered to contact the surface. The control system 113 receives data identifying characteristics of the grape surface (e.g., user input indicating the type of surface, user input indicating surface characteristics, and/or output from sensors which measure characteristics of the sample bearing surface). Based on the received data, the control system 113 determines a pressure to be applied by the seal assembly 112 to the grape surface. As discussed above, the control system 113 can include a program with a stored list (e.g., in a database) of desire surface pressures associated with different surfaces to be sealed. In some systems, determining the pressure includes accessing the database of surfaces and associated pressures.

The control system 113 sends a control signal from the control system 113 to the actuator 120 to operate the actuator to press the cavity assembly 118 against the grape surface until the pressure is achieved. The control system 113 also receives data from the force gauge 122 which measures the force actually being applied to the surface enables a feedback loop for precise control of the applied pressure. Application of the pressure substantially seals the open side of the cavity against the grape surface without penetrating the skin.

A solvent is supplied to the cavity 126 through the fluid inlet line 138 and the inlet 156 to extract the sample from the grape surface. The extracted sample is removed from the cavity 126 through outlet 158 and the fluid outlet line 140 before being transferred to the mass spectrometer 210 or another sample analysis device.

The systems and methods described in this disclosure can be used to effectively employ the high sensitivity, high specificity and high throughput analysis of analytes of interest provided by mass spectrometry while simplifying the sample preparation required before mass spectrometer analysis can begin. These systems and methods can reduce the issues such as selecting the column (size and material), gradient profiles, run times, dilution ratios, sample concentrations, etc. that often make liquid chromatography challenging and costly. These systems and methods can also significantly reduce the run times (e.g., ranging from ~10 minutes to more than 60 minutes) associated with other liquid chromatography methods, thus reducing the associated costs and waste disposal issues.

The systems and methods described in this disclosure often require only a few minutes for sample extraction and analysis. For example, the development of a TLC plate identifies sample spots and extraction of the sample to the mass spectrometer typically takes less than one minute while consuming less than 1 ml of solvent.

FIGS. 8A-C illustrate operation of a surface extraction interface system 800 having a nitrogen purging system. The surface extraction interface system 800 uses an air/liquid backflush system to clean out an extraction head 137. FIGS. 8A-C show plumbing enabling back flushing of the extraction head 137 with residual solvent and nitrogen gas. In detail, FIGS. 8A-C show a surface extraction interface system 800 including a solvent delivery system 811, a MS detection system 210, and a surface extraction system 801 having a 6 port valve 870. The 6-port valve 870 enables connection of the extraction head 137 of the surface extraction system 801 to a source of nitrogen gas, the solvent delivery system 810, and the MS detection system 210. In operation, the 6 port valve 870 uses a single plugged port 872 and 5 open ports 871 to enable, in the configuration of FIGS. 8A and 8C, purging of the sample return line (elution line 881), and, in the configuration of FIG. 8B, both delivery of a solvent flow 888 from the solvent delivery system 811 to the sample 810 and delivery of the solvent flow 888 from the sample 810 to the MS detection system 210.

In FIG. 8A, the extraction head 137 is disengaged from the sample 810 and the elution line 881 is filled with N2, after purging the previous sample. In FIG. 8B, the extraction head 137 engages sample 810 with contact pressure control. Solvent flow 888 from the delivery system 881 flows through or over the sample surface 810 and delivers extracted analytes to the MS detection system 210. In FIG. 8C, the extraction head 137 is disengaged from the sample and the nitrogen purge line 881 is opened and flushes the line with previous solvent first and nitrogen gas second—this clears out the capture frit and readies the system 800 for the next sample.

Figure 15A:
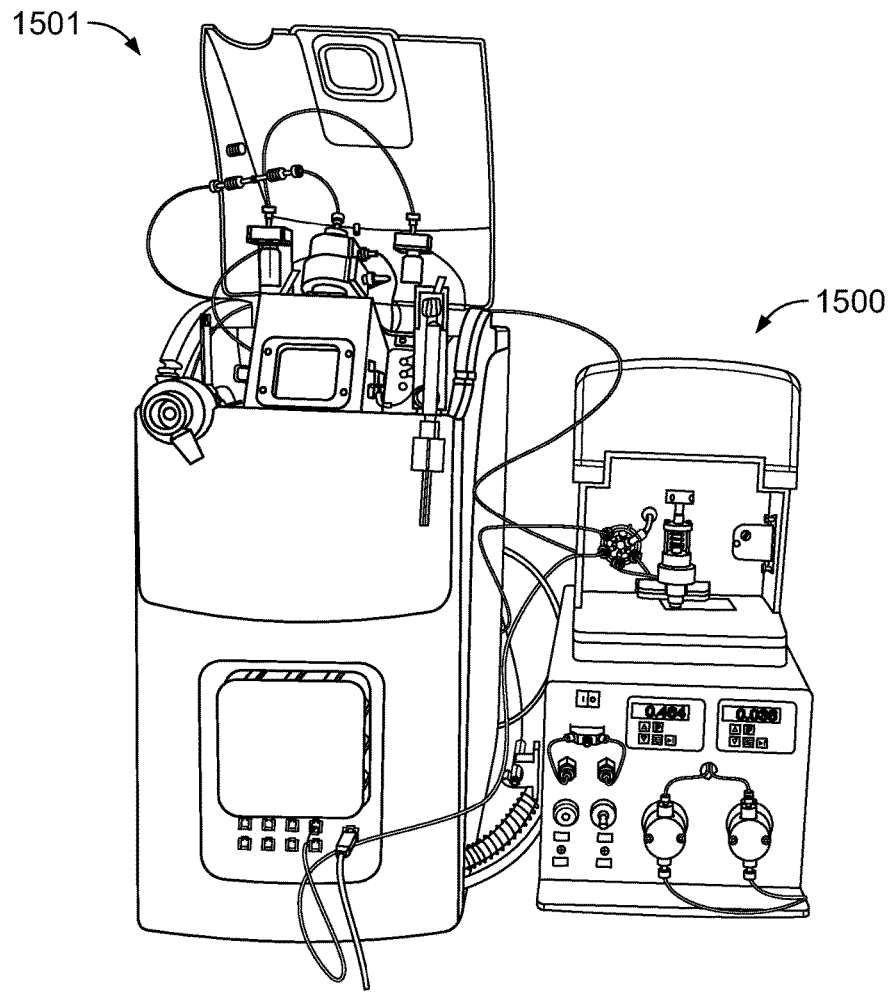
FIGS. 15A and 15B are photographs of a sample analysis system and a fingerprint on filter paper prepared for sample analysis.
Figure 15B:
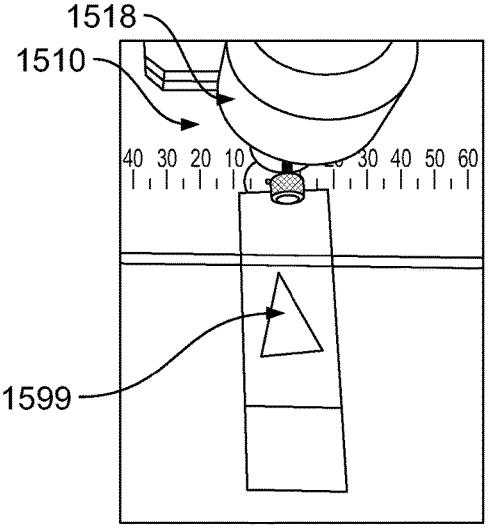

FIGS. 9A-16B show the results of analyzing samples extracted from a variety of surface types, including dried blood spot cards (FIGS. 9A and 9B), thin tissue sections, for example whole body mouse sections (FIGS. 11A and 11B), test swabs (FIG. 13), and fingerprints on filter paper (FIGS. 15A and 15B). Varies other types of surfaces may be sampled from, for example, metal and plastic surfaces.

Figure 9A:
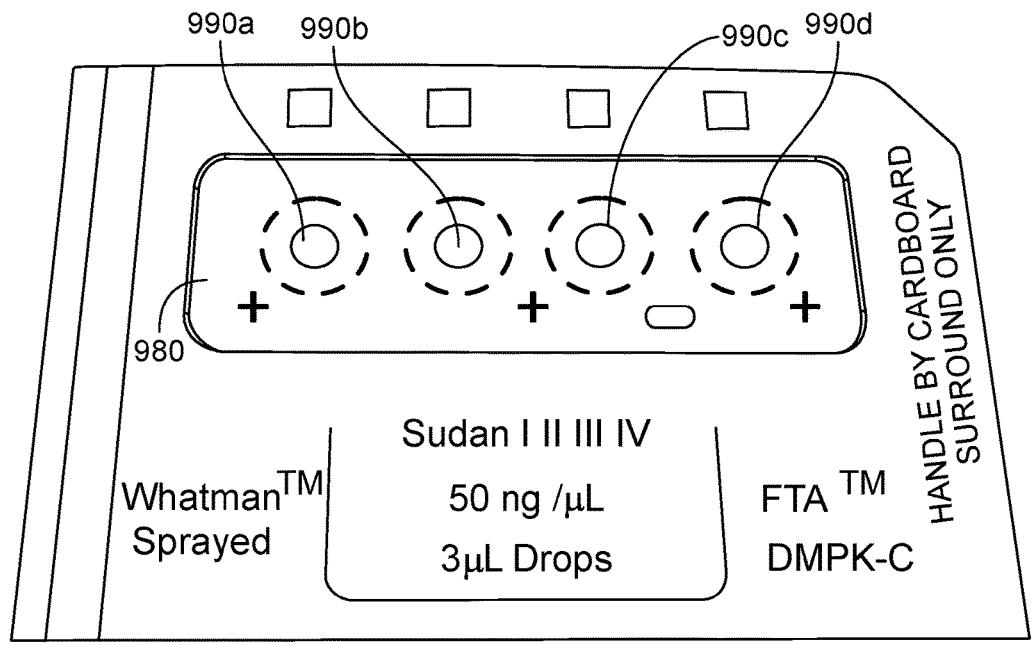
FIGS. 9A and 9B are photographs of a sampling plate having dye samples before and after sample surface extraction, respectively.
Figure 9B:
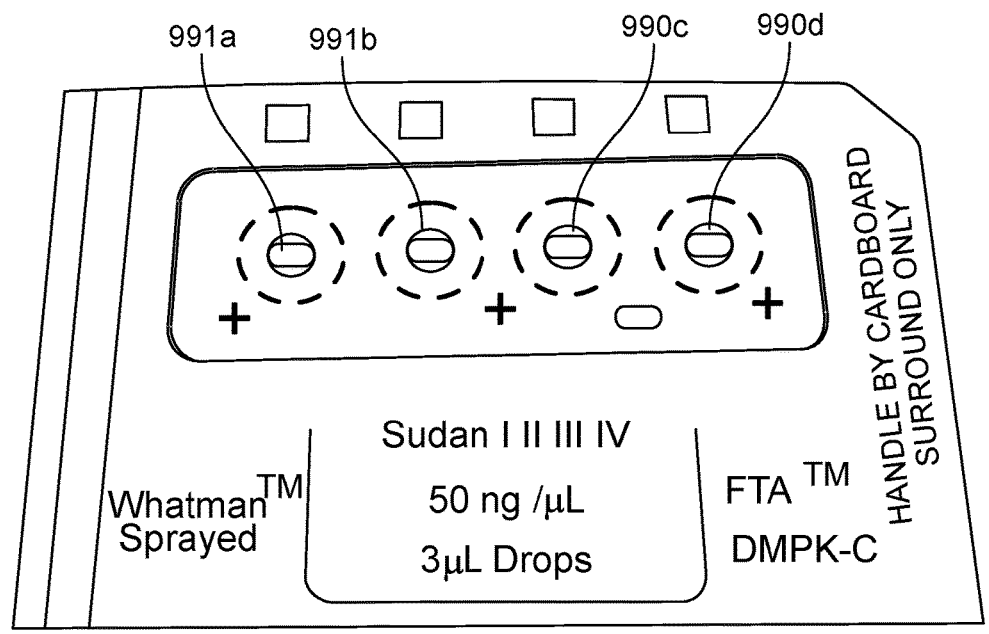

FIGS. 9A and 9B are photographs of a sampling plate having dye samples before and after sample surface extraction, respectively. FIG. 9A shows a dried blood spot card 980 having four identical drops 990a-d of Sudan red dye mixture. FIG. 9B shows the dried blood spot card 980 after a surface extraction interface system 100 has collected four samples from each of the target regions 991a-d corresponding to the location of the four identical drops 990a-d of Sudan red dye mixture.

Figure 10:
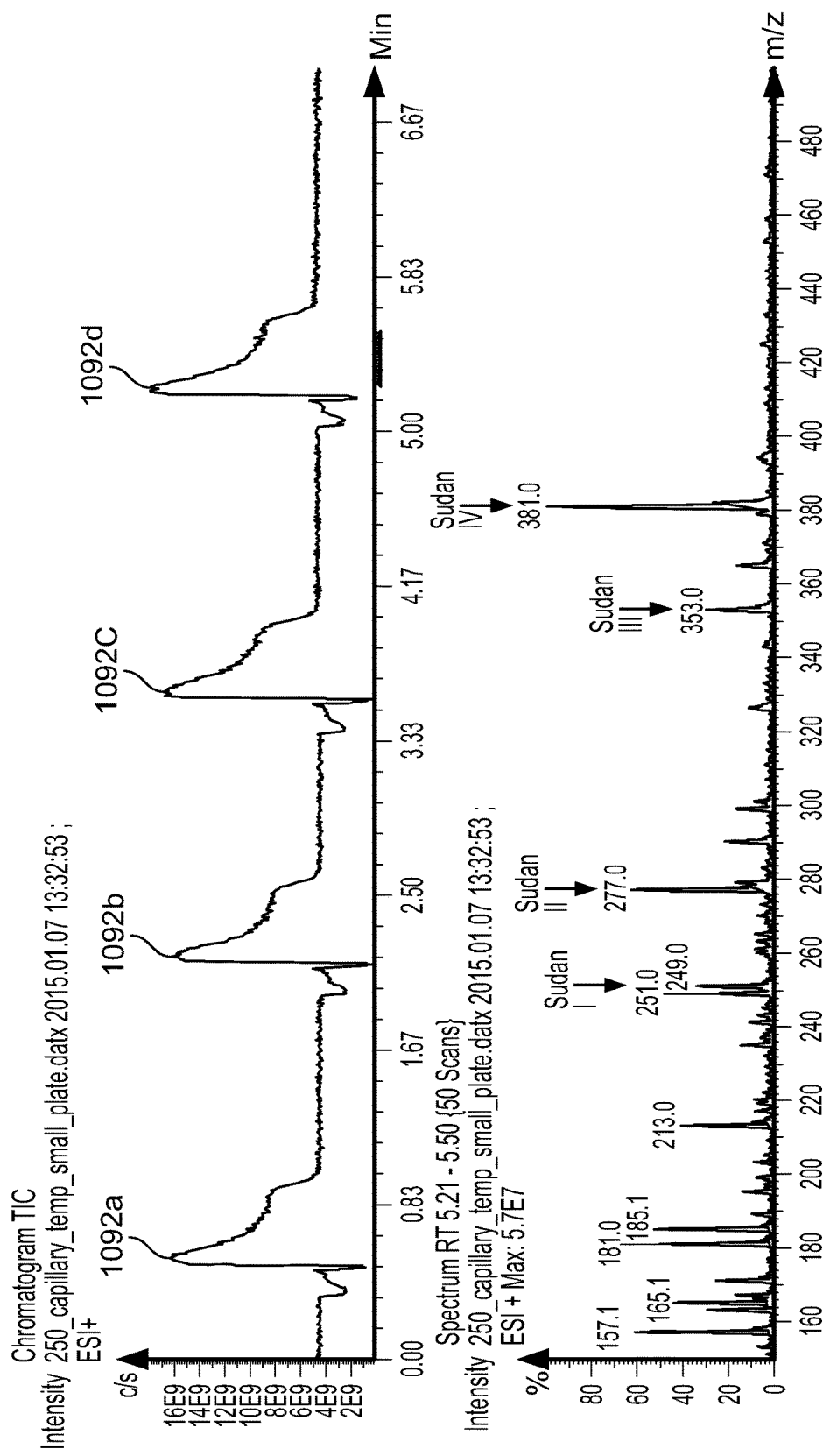
FIG. 10 is a graph showing four identical FIA analysis peaks for the four spots showing dye I, II, III, and III of FIGS. 9A and 9B.

FIG. 10 is a graph showing four identical FIA analysis peaks for the four spots showing the sudan dyes I, II, III, and III of FIGS. 9A and 9B detected over the sampling time.

Figure 11A:
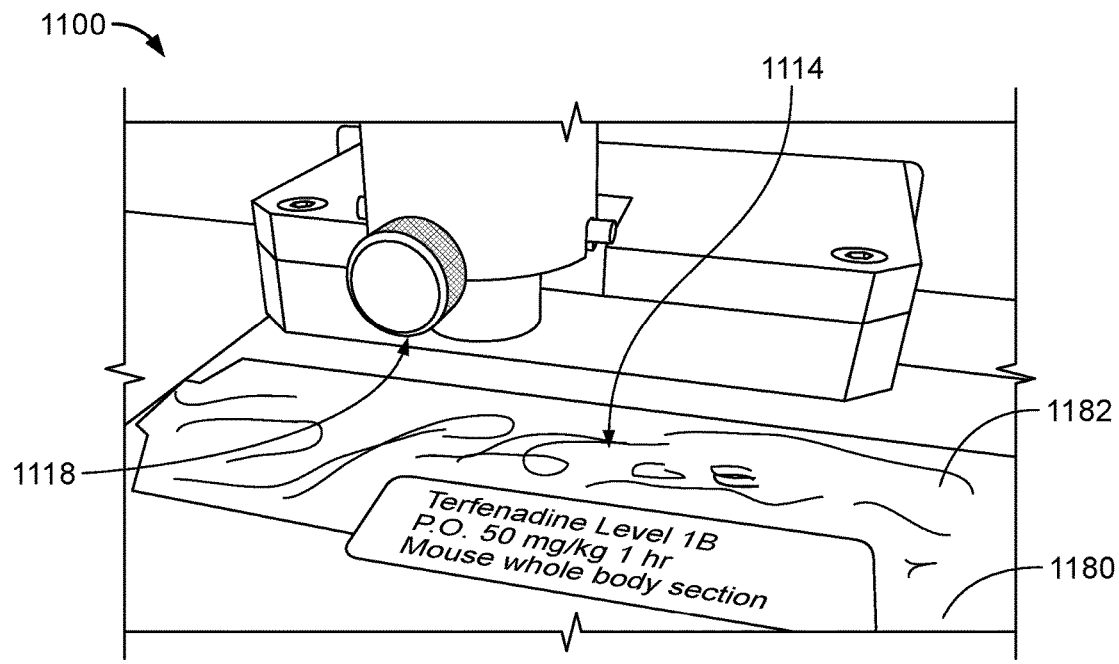
FIGS. 11A and 11B are photographs of a surface extraction interface system before and during, respectively, of a collection process from a whole body thin tissue sample.
Figure 11B:
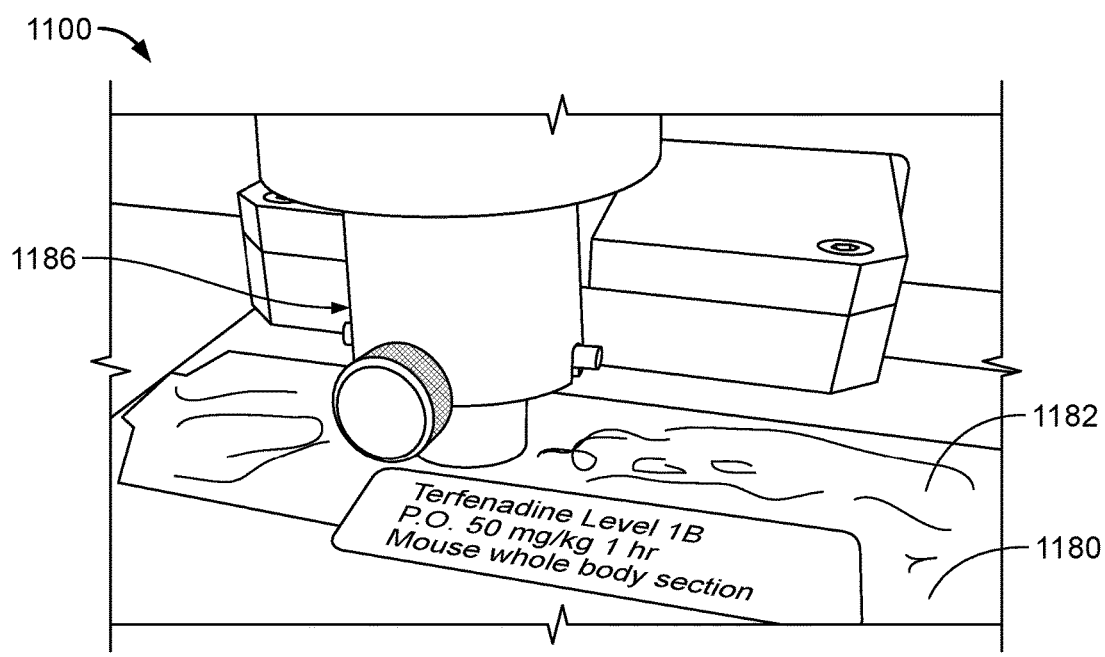

FIGS. 11A and 11B show a surface extraction interface system before and during, respectively, of a collection process from a whole body thin tissue sample FIG. 11A shows a surface extraction interface system 1100 having a cavity assembly 1118 and cavity (not visible) and a sample plate 1180 with a whole body thin section tissue sample 1182. The surface extraction interface system 1100 includes a laser guide 1114 to align the cavity assembly 1118 with a target section of the tissue sample 1182. FIG. 11B shows the cavity assembly 1118 lowered toward the sample plate 1182, placing the cavity (not shown) in sealing contact with a target section of the whole body thin section tissue sample 1182. Four different organ tissue samples were collected from the surface of the tissue sample 1182 and analyzed using MS, as shown in FIG. 12.

Figure 12:
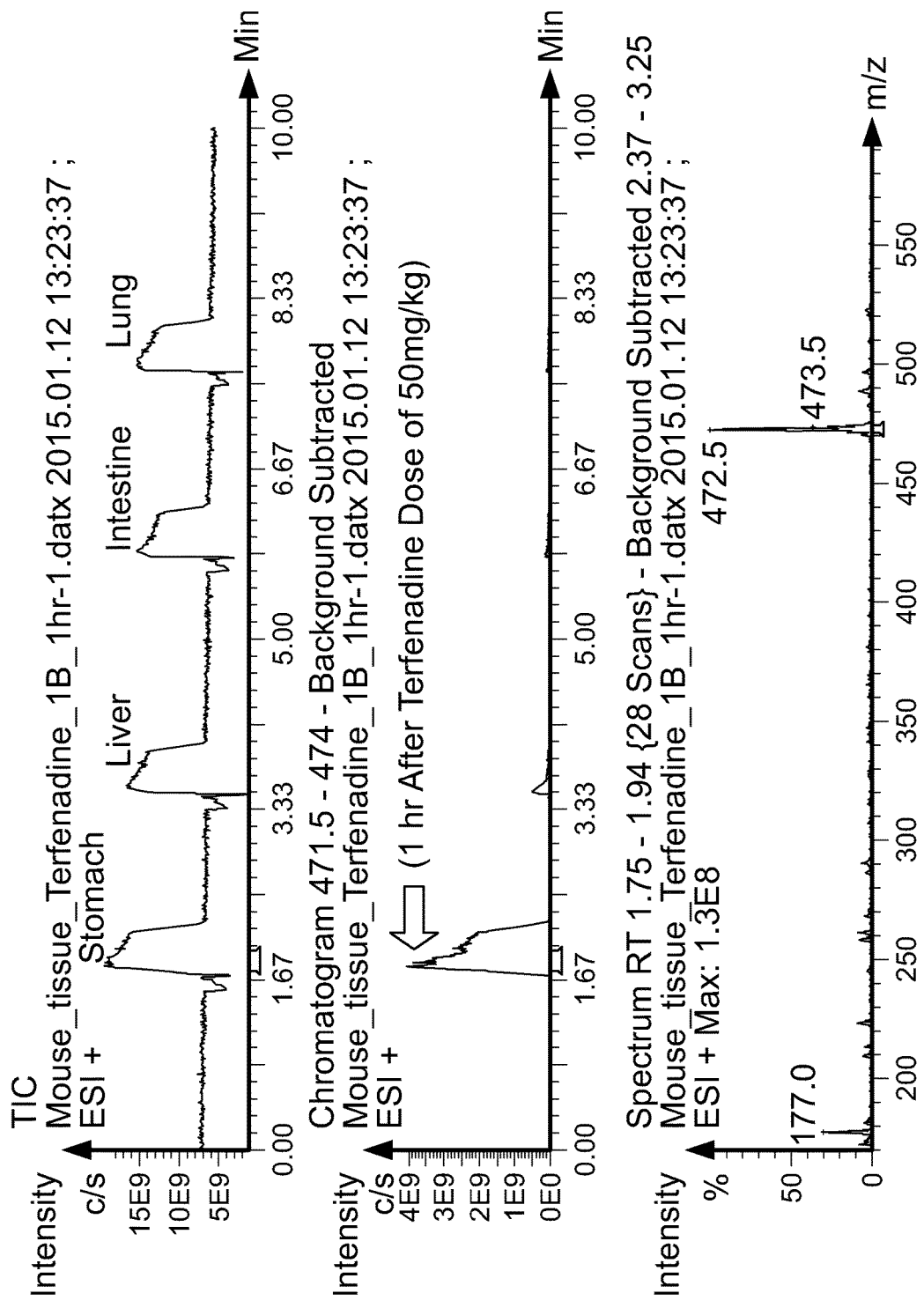
FIG. 12 is a graph of mass spectrometry data of a surface sample collected at various locations on a whole body thin tissue sample after ingestion of Tefenadine.

FIG. 12 is a graph of mass spectrometry data of a surface sample collected at various locations of a whole body thin tissue sample after ingestion of Tefenadine. FIG. 12 shows data corresponding to the four surface samples taken from the whole body thin section tissue sample 1182 of FIG. 11. The four surface samples correspond to the stomach, liver, intestines, and lung of the mouse from which the whole body thin section tissue sample 1182 was taken. The mouse being sampled ingested a dose of 50 mg/kg of Terfenadine prior to collection of the tissue sample, and the data of FIG. 12 shows that a detectable amount of Terfenadine was present in the sample of the stomach tissue.

Figure 13:
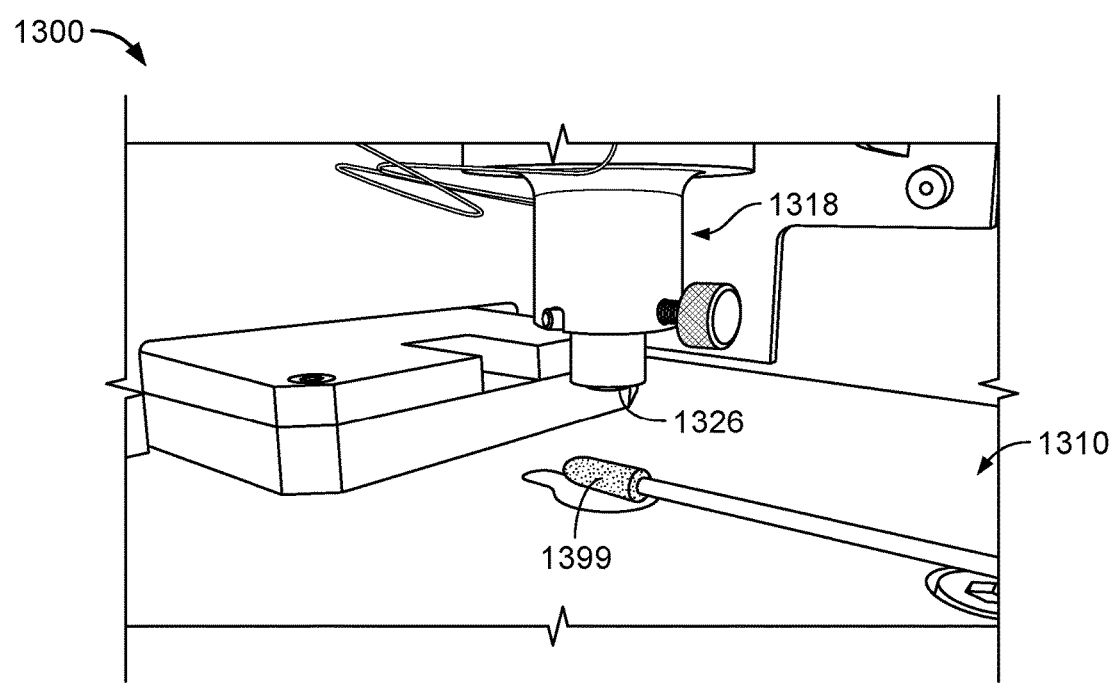
FIG. 13 is a photograph of a surface extraction interface system configured to collect a sample from a test swab.

FIG. 13 is a photograph of a surface extraction interface system configured to collect a sample from a test swab. FIG. 13 shows a surface extraction interface system 1300 including a cavity assembly 1318 with a cavity 1326 (visible only as a cavity wall), and a test swab 1399 positioned of a sample plate 1310. In operation, the surface extraction interface system 1300 descends the cavity assembly 1318 until the cavity 1326 contacts the test swab 1399 and forms a seal. In this experiment, the results of which are shown in FIG. 14, the test swab contained chocolate and, therefore, MS results from a sample are expected to detect theobromine and caffeine.

FIG. 14 is a graph of mass spectrometry data of a surface sample extracted from a test swab. FIG. 14 shows MS data from a surface sample collected from the test swab 1399 of FIG. 13. The graphs of FIG. 14 indicate that theobromine and caffeine were presented in the surface sample collected from the test swab 1399.

FIGS. 15A and 15B show a sample analysis system and a fingerprint on filter paper prepared for sample analysis. FIG. 15A shows a surface extraction interface system 1500 attached to a mass spectrometry system 1501. FIG. 15B shows the surface extraction interface system 1500 including a cavity assembly 1518 with laser target region indicator and a sample plate 1510 having thereon a sample section of filter paper 1599 with a pressed fingerprint of a cocaine user.

Figure 16A:
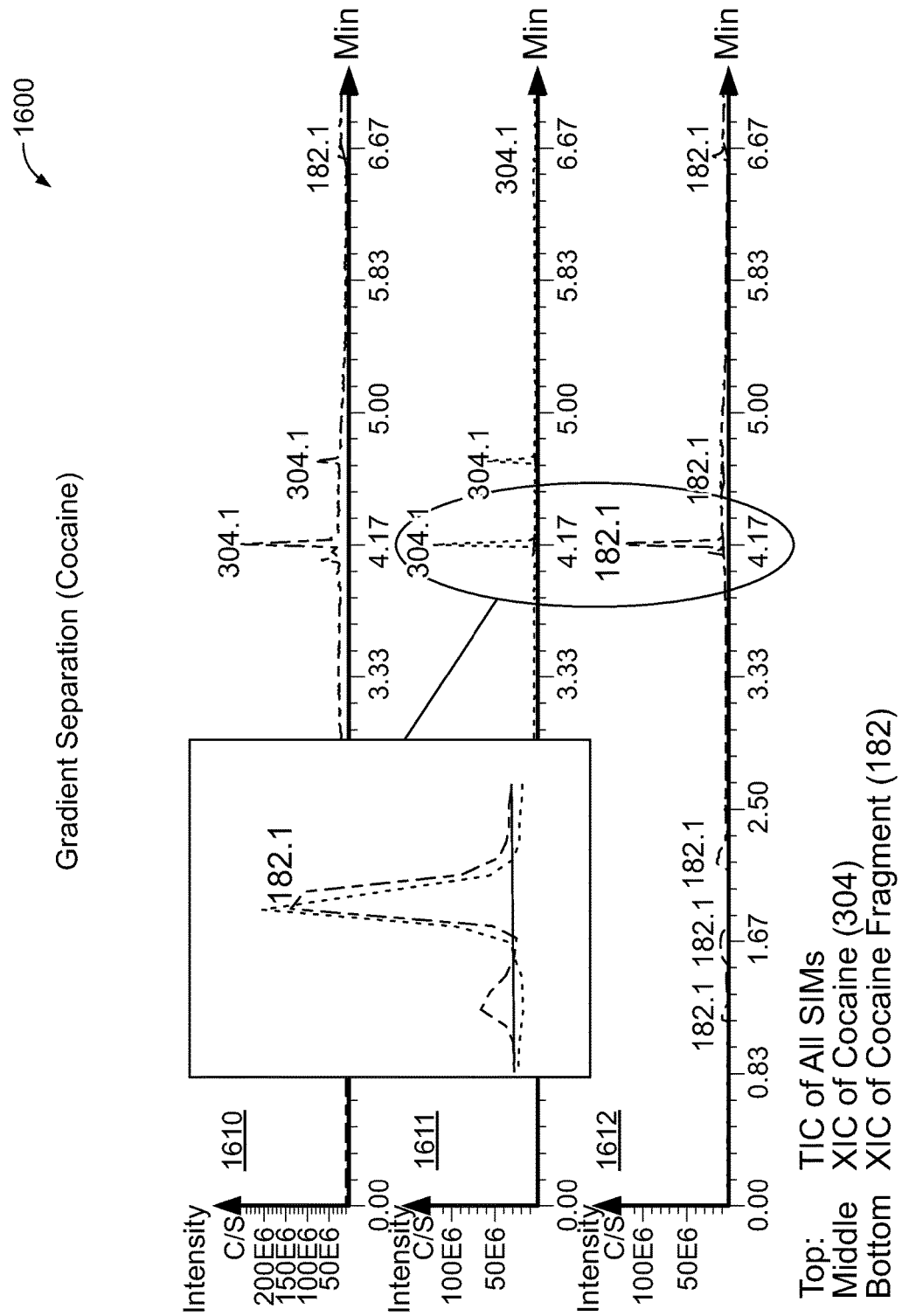
FIGS. 16A and 16B are mass spectrometry data of a surface sample collected from filter paper having a fingerprint of a cocaine user.
Figure 16B:
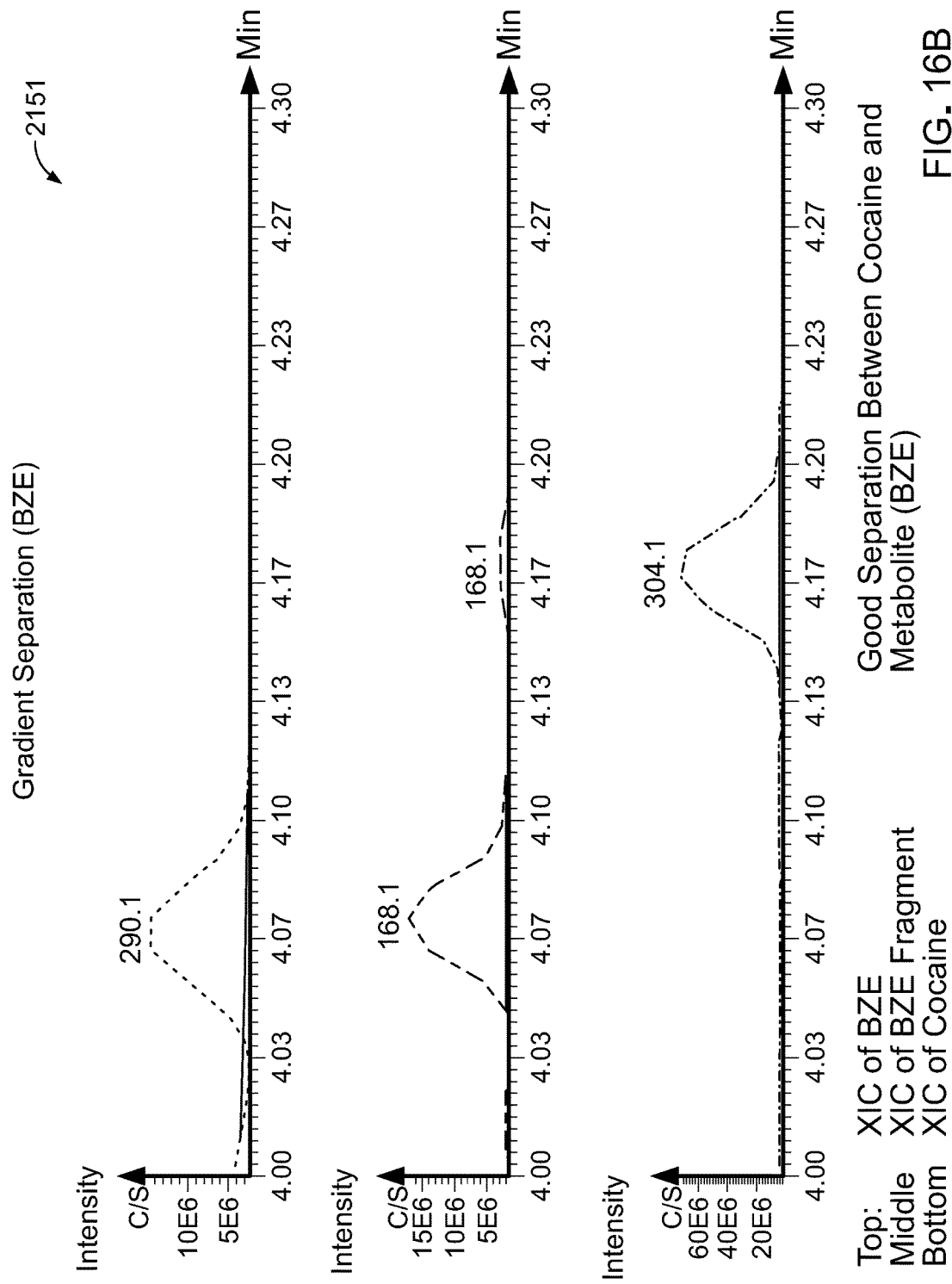

FIGS. 16A and 16B are mass spectrometry data of the surface sample collected from filter paper 1699 having a fingerprint of a cocaine user. The results 1600 shown from the Cocaine analysis of the finger sweat from a cocaine user after taking a fingerprint (finger swab) and having the sweat absorb into the filter paper 1699. Top trace 1610 is total ion chromatogram, middle trace 1611 is extraction ion chromatogram from cocaine, and lower trace 1612 is extracted ion chromatogram of m/z 182.1, a known fragment of cocaine under in source fragmentation conditions. When running the analysis and comparing to analytical standards placed on similar paper cutouts, the presence of cocaine can be confirmed by both retention time and in source fragmentation. FIG. 16B shows data 1601 indicating detection of a physiological metabolite of cocaine (BZE) that is well separated from the cocaine and may be used additionally to identify cocaine use in finger sweat.

Figure 17:
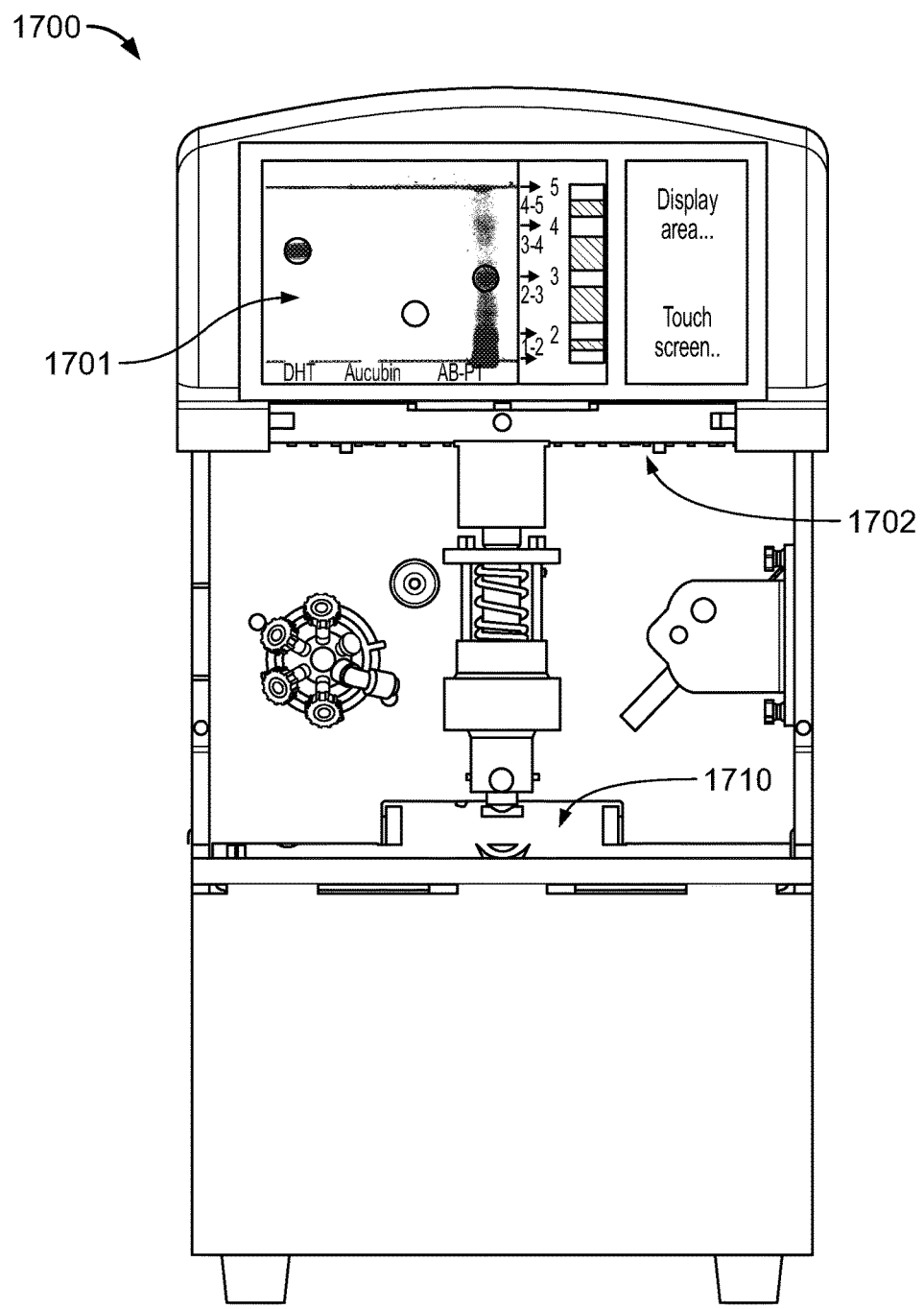
FIG. 17 is an illustration of a surface extraction interface system having manual and automatic sample location recognition.

FIG. 17 is an illustration of a surface extraction interface system having manual and automatic sample location recognition. FIG. 17 shows a surface extraction interface system 1700 having manual and automatic sample location spot recognition. The surface extraction interface system 1700 includes a touch screen 1701 interface which enables the system 1700 to run a stand-alone application or operate as a slave to an attached MS system (210 of FIG. 7). The surface extraction interface system 1500 includes an illumination system 1702 which may include, for example two UV lamps of different wavelengths and a camera system for capturing the target plate 1710. The illumination system 1502 enables the surface extraction interface system 1700 to provide both manual control and automatic control. For example, a user can manually translate the sample plate and extraction head (their motion is detailed in FIGS. 18A and 18B) to extract a surface sample from a desired target surface section. In manual operation, the user can either directly visually align the extraction head over the sample using, for example, a laser target indicator appearing on the sample, or the user can observe the orientation of the sample and extraction head using a the touch screen 1701 and camera system. Alternatively, the user can instruct the surface extraction interface system 1700 via the touch screen 1701 to sample from a target region identified by the user on the touch screen 1701 or instruct the surface extraction interface system 1700 to automatically identify preferred regions of the sample and collect surface samples from the identified regions.

Figure 18A:
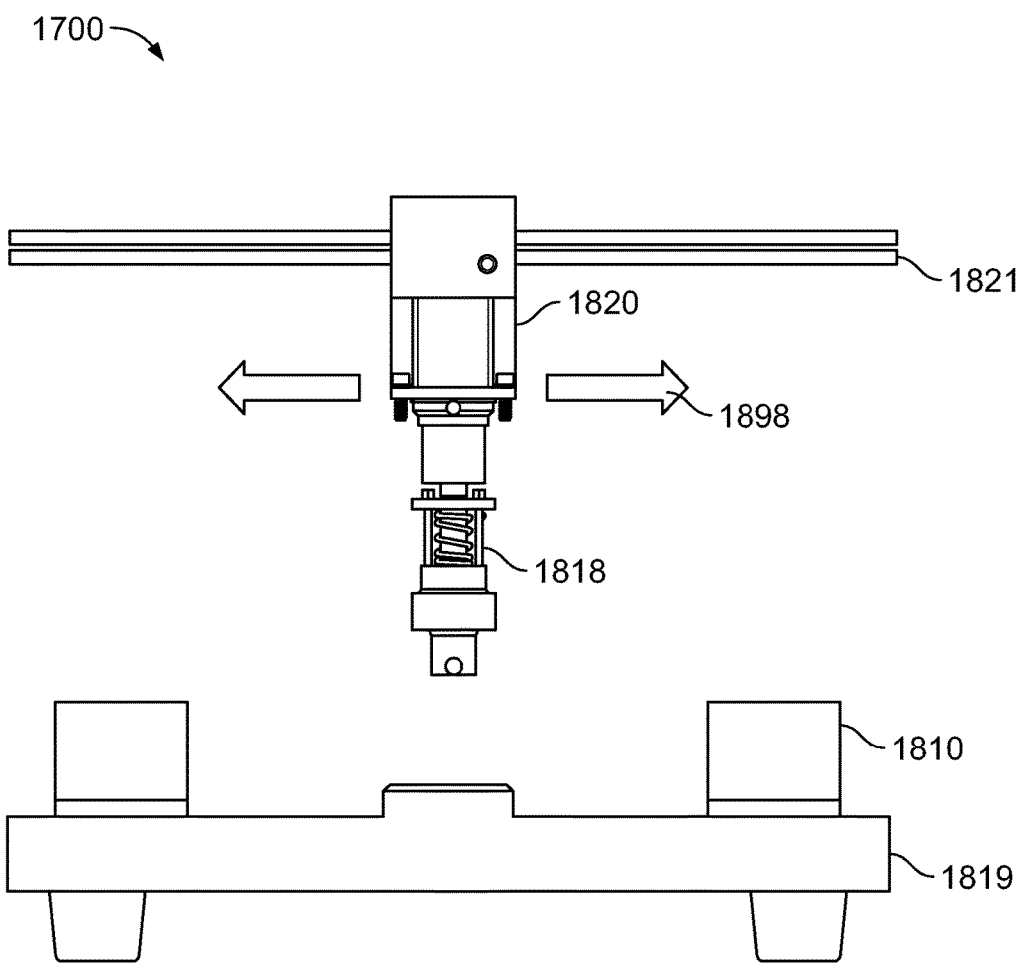
FIGS. 18A and 18B are diagrams of single-axis translation of a head assembly and base assembly, respectively, of a surface extraction interface system.
Figure 18B:
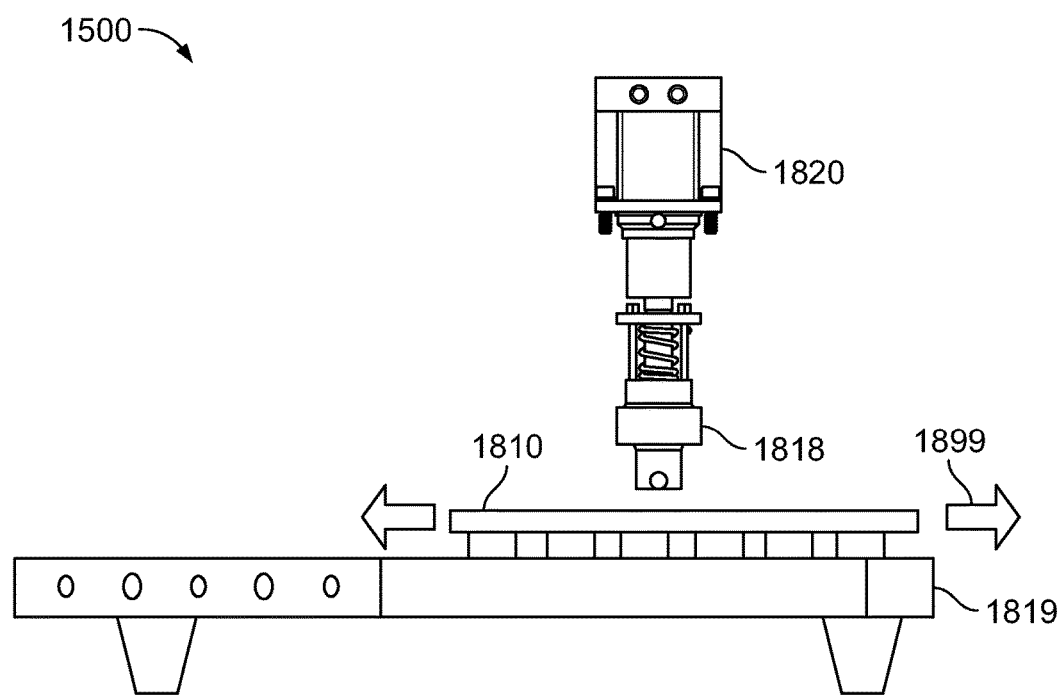

FIGS. 18A and 18B are diagrams of single-axis translation of a head assembly and base assembly, respectively, of a surface extraction interface system. The surface extraction interface system 1700 moves positions the cavity assembly 1818 over a desired region of the a sample on the sample plate 1810 by moving the head assembly 1820 along a single direction, and moving the sample plate 1810 in a perpendicular direction. FIG. 18A shows left to right movement of the head assembly 1820 using two rails 1621 as a guide. FIG. 18B shows front to back movement of the base assembly 1810 on base rails 1819.

Figure 19:
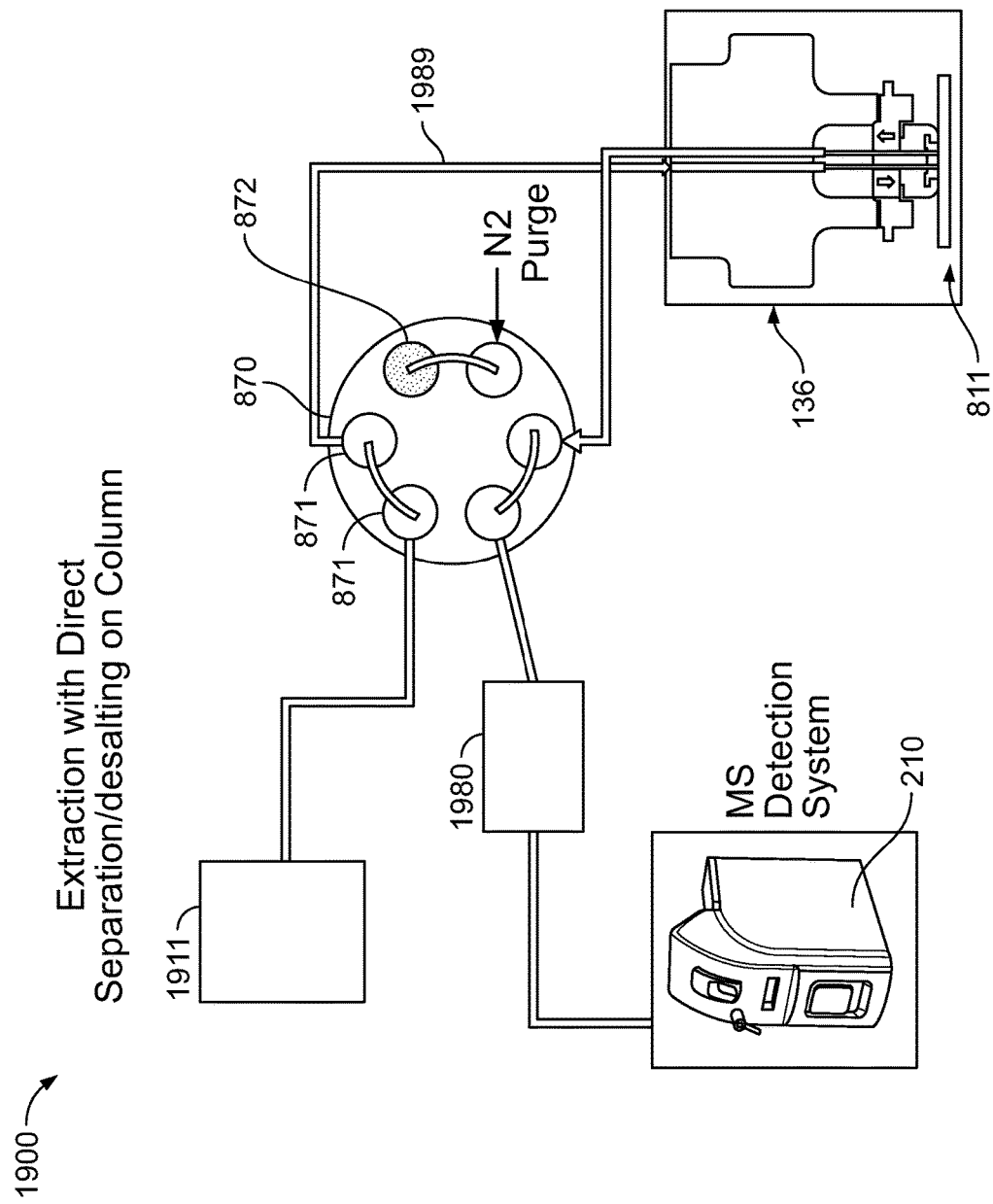
FIG. 19 is a diagram of a surface extraction interface system including direct separation and desalting on a column.

FIG. 19 is a diagrams of a surface extraction interface system including direct separation and desalting on a column. Differences exist between TLC plates as a surface of interest and other surfaces such as a leaf or other plant material, dried blood spots, whole body or single organ thin section tissues, swabs, etc. For example, on a TLC plate, the multitude of analytes present in the sample has already be simplified by separating the analytes by space prior to the surface extraction due to the TLC development. Other surfaces however may show a multitude of analytes and/or a significant amount of matrix components in addition to the analyte(s) of interest. In these cases, it is beneficial for both sensitivity and selectivity to have a separation of analytes and analytes from matrix as extracted from the surface of interest. FIG. 19 shows such a set-up for the removal of matrix components e.g. salts. Similar example set-ups can include, generally, another separation dimension if analytes are already pre-separated (such as on a TLC or cellulose plate that has been developed) and thereby add a different dimension of separation based on different physical properties of the analytes. The system of FIG. 19 may include, for example, C18 separation on a short HPLC column following a partial separation on Silica gel 60 TLC plates. Alternatively, a strong cation exchange chromatography (SCX) could be following a C18 separation on TLC plates.

FIG. 19 shows a surface analysis system 1900 including a high-pressure liquid chromatography (HPLC) column 1780 in the workflow, a solvent delivery system 1911, and a MS detection system 210. The HPLC may be, for example, a 2.1×50 mm C18 column. This configuration requires contact pressure control at the sampling device to prevent leakage of solvent due to increased backpressure or an alternative loop injection method.

Addition of the HPLC column 1980 to the surface analysis system 1900 increases backpressure in the extraction line 1989 due to resistance of the particles in the HPLC 1980 used for separation of analytes and the extraction head 137 can increase contact pressure to continue to seal off the sample surface 110 and prevent leakage during the extraction. Using a force gauge (122 of FIG. 2) the surface analysis system 1700 precisely controls the contact pressure in consideration of the backpressure generated and the sample surface 810 of interest and accommodates a significant amount of back pressure in the 20 to 1000 psi range (as measured at the pump head in the solvent delivery system 1911).

For example, given a peptide sample deposited onto a TLC plate, the surface analysis system 1900 can make contact with the surface 111, flush the analyte from the surface onto an HPLC column 1980. This, for example, generates an isochratic chromatogram that shows a single early eluting peak at 0.55 min that represents salts and other matrix components, a broader, early eluting peak at 0.89 min that represents the analyte of interest (as determined by MS, FIG. 20, m/z 1063.55), and additional later eluting compounds that are also present in the sample (Rt>1.5 min).

Figure 20:
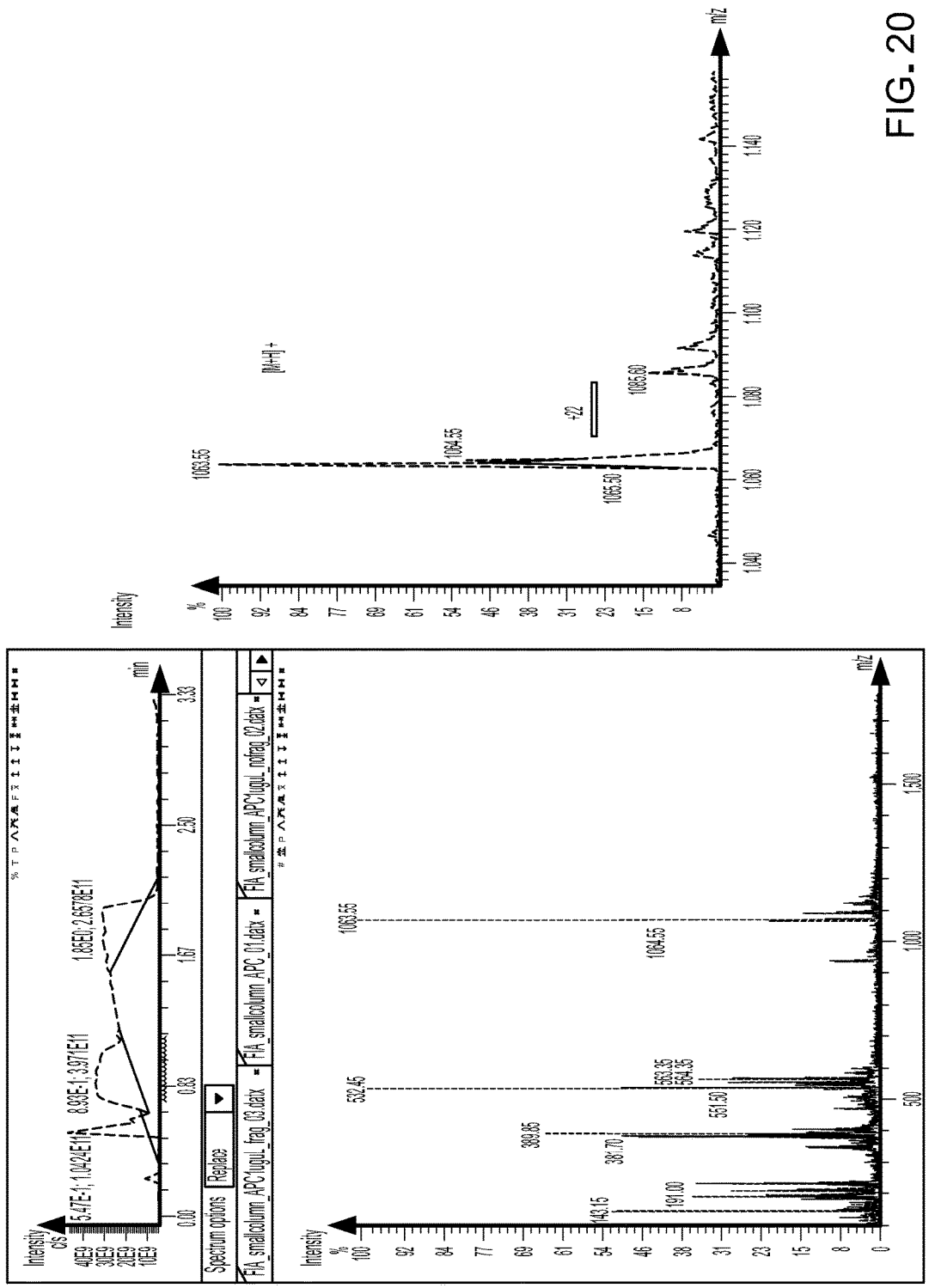
FIG. 20 is an example of a peptide sample extracted from a TLC plate and desalted and separated on a short chromatography column.

FIG. 20 is an example of a peptide analysis after desalting in such a system from a TLC surface.

Figure 21A:
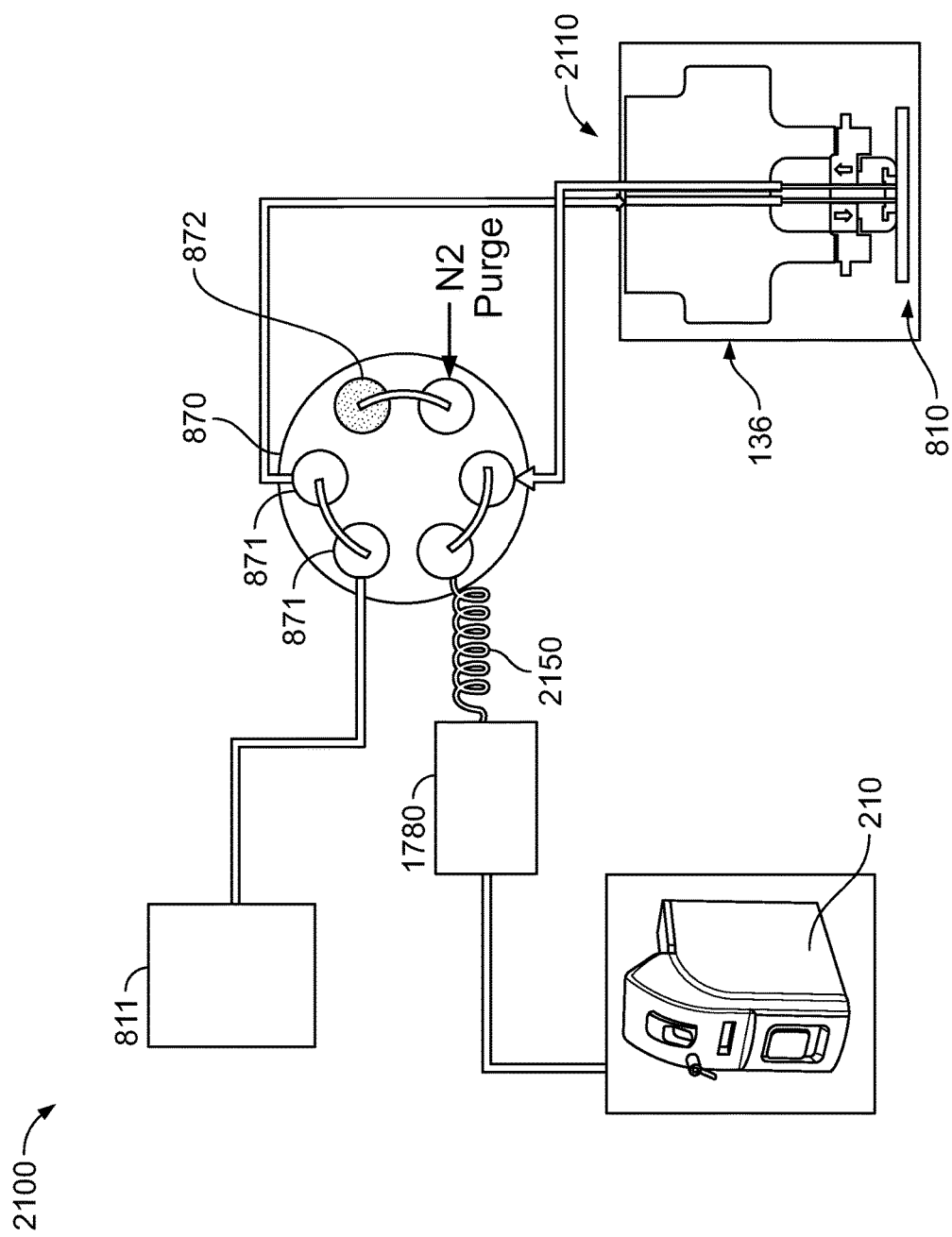
FIGS. 21A and 21B are diagrams of a surface extraction interface system with sample loop.
Figure 21B:
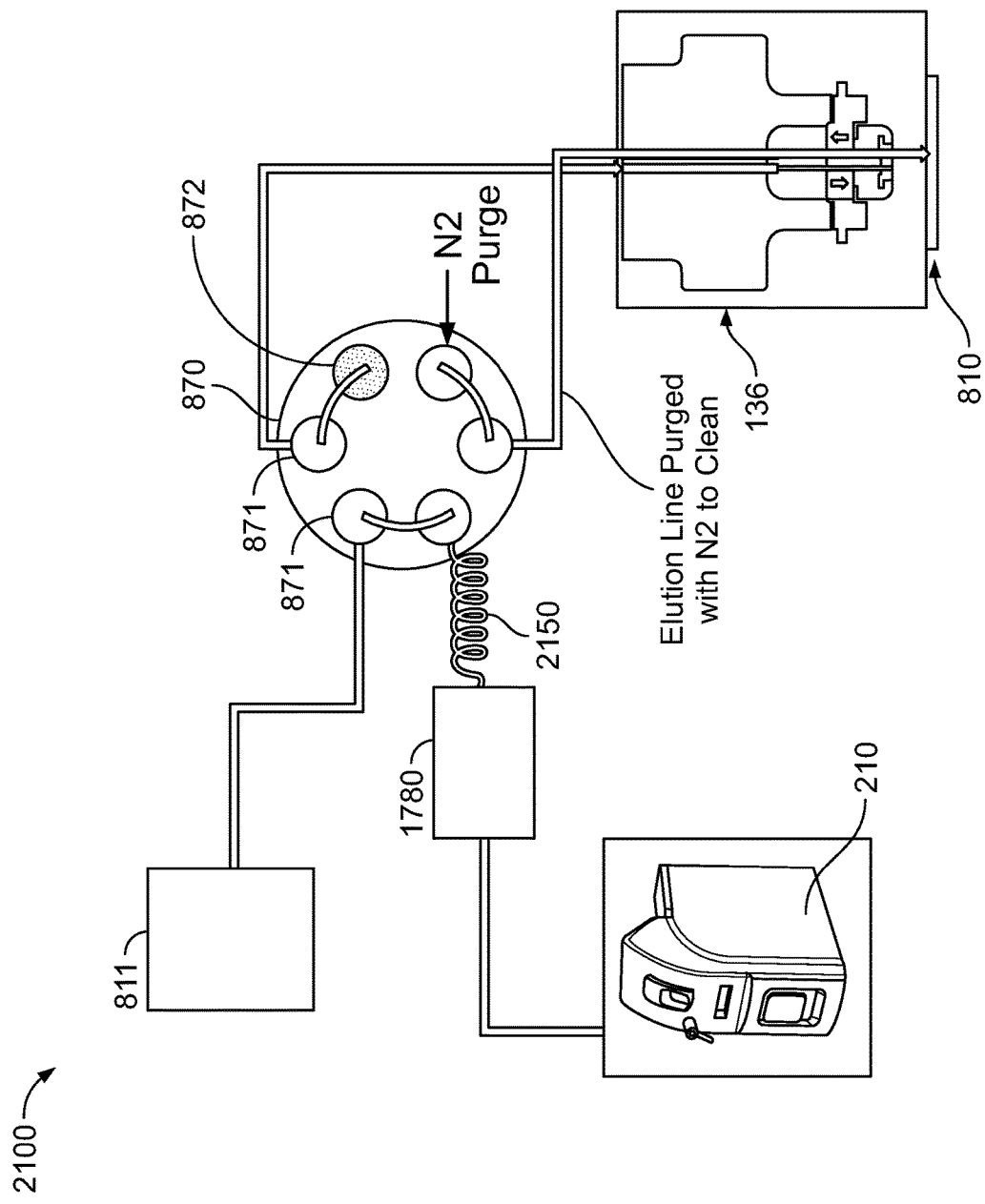

FIGS. 21A and 21B are diagrams of a surface extraction interface system with sample loop. The surface analysis system 2100 is modified to extract analytes form the surface 810 and, instead of moving them onto the HPLC column 1780 immediately, reduces the flow rate and slowly moves the extraction plug of solvent into a sample loop 2150 (which may be, for example 1 uL-100 mL). Due to the lower flow rate, the backpressure will be limited and the force gauge (122 of FIG. 2) is able to counteract the pressure on the surface and provide a seal on the surface 810. This is very useful for small size column particles, such as 3 um particle columns, or for columns of larger length, such as 10-20 cm columns. Using a properly plumbed 6 port valve 870 the system 2100 will then, during the clean phase of the surface extraction device 2110, revert to normal flow rates and hence higher back pressure and move the extraction plug of solvent from the loop onto the HPLC column 1780 for separation and further analysis.

In FIG. 21A, an isochratic or binary pump of the solvent delivery system 811 is programmed to run at lower flowrate (lower back pressure) to move extracted sample into the loop 2150 only (1 uL to 100 mL). FIG. 21B shows the plate express extraction head 137 disengages from sample 810 for standard cleaning process. At the same time, the system 2100 delivers a gradient to analyze the sample by LC-MS at now higher/normal flow rates and higher back pressure.

Figure 22A:
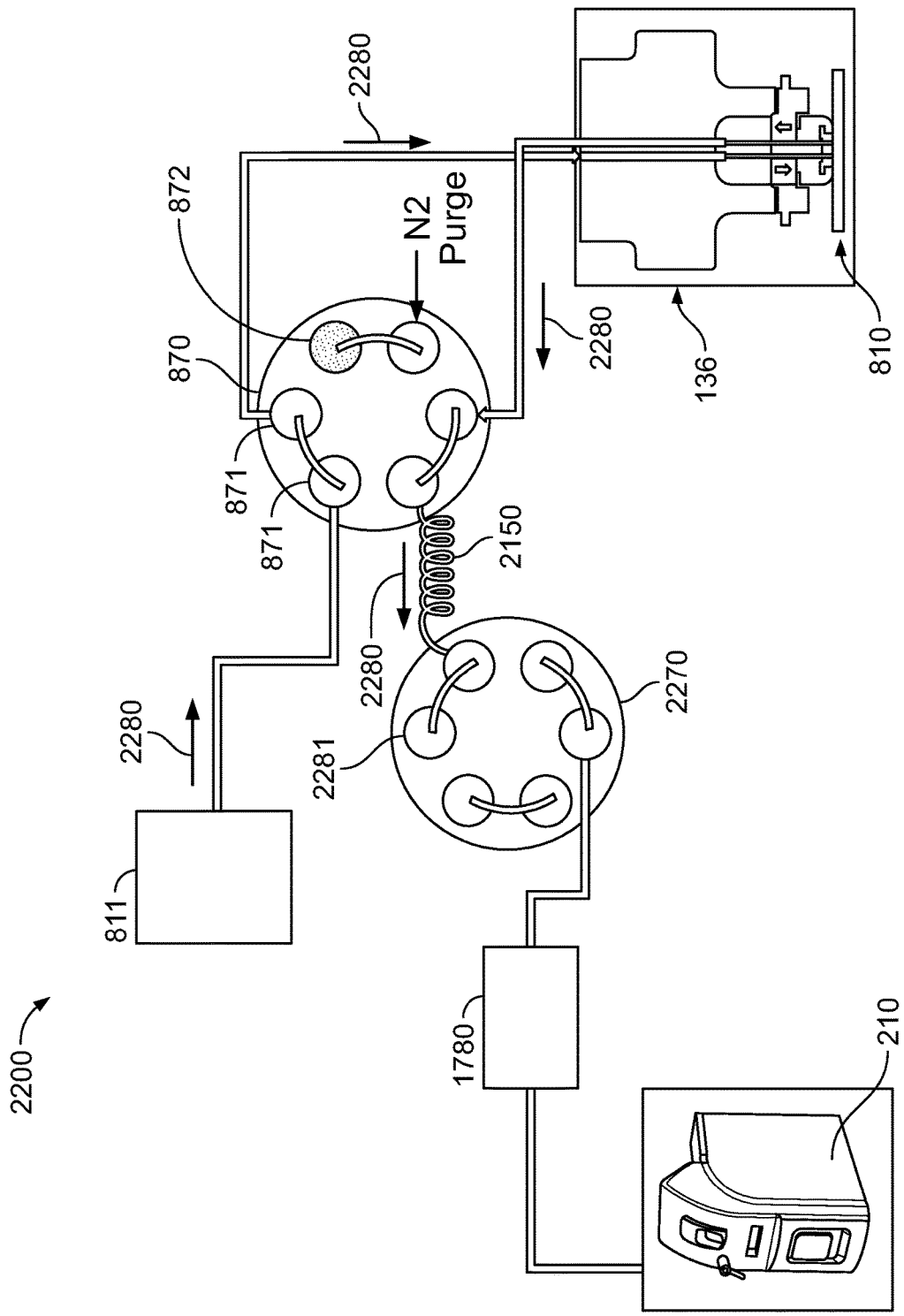
FIGS. 22A and 22B are diagrams of a sample analysis system with a sample loop and column.
Figure 22B:
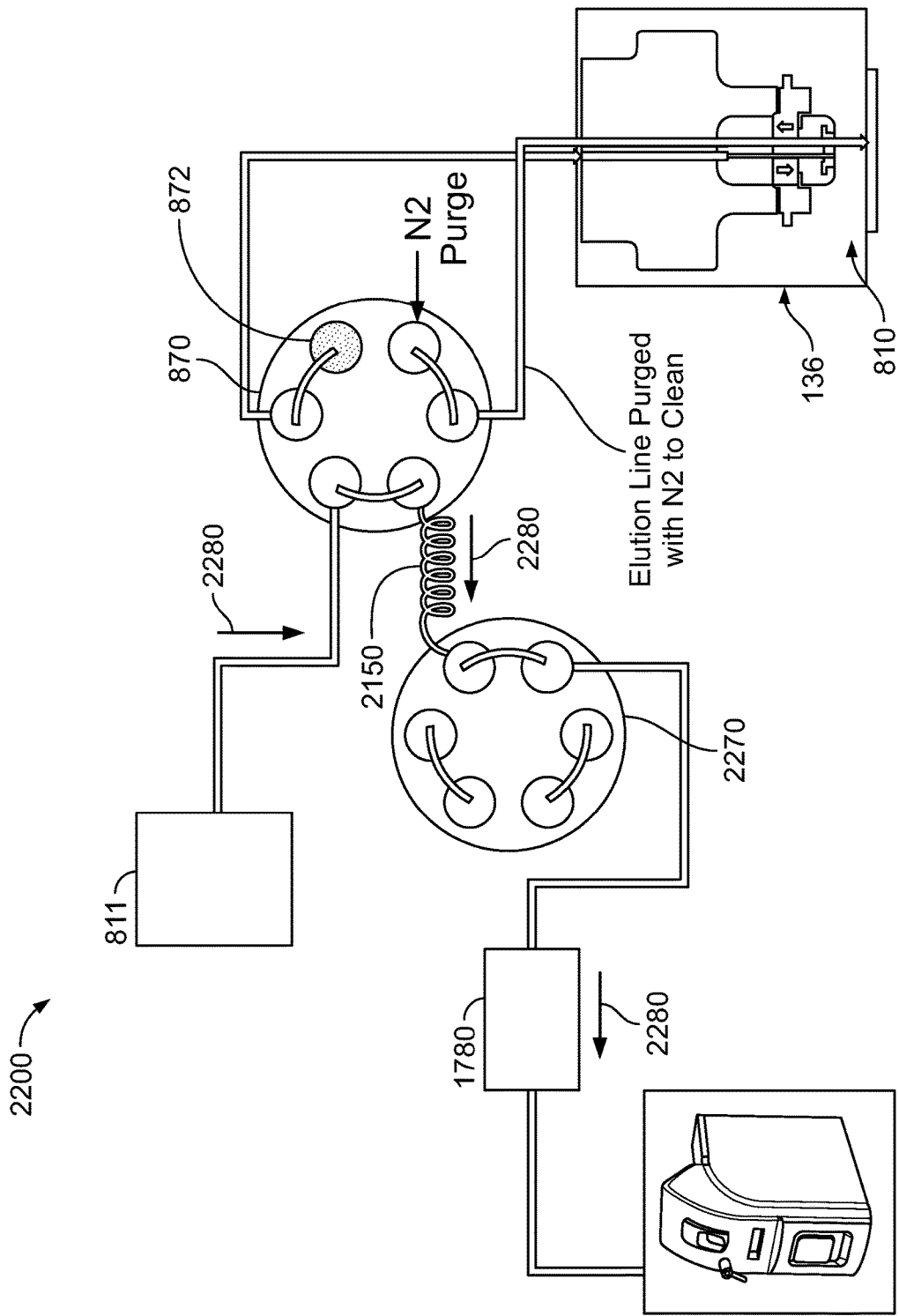

FIGS. 22A and 22B are diagrams of a sample analysis system with a sample loop and column. The example system 2200 shown requires the plumbing of a second 6 port valve 2270 or a single 10 port valve (not shown). In injector mode, as shown in FIG. 22A, the extraction stream 2280 will first flow over the surface 810 for extraction and into the loop 2150 connected to a waste line 2281 at lower backpressure. The pump of the solvent delivery system 811 runs at normal flow with the loop open to the waste line 2281, resulting in low back pressure and a delivery of 1 uL to 100 mL. In FIG. 22B, the solvent plug 872 is placed in the loop (at a time calculated by time and volume of solvent deliver using the known tubing sizes involved), and the system 2200 switches the two 6 ports valves 870, 2270 simultaneously to connect the gradient pump of the solvent delivery system 811 directly to the loop and HPLC column 1780 and a standard LC run commences (injector mode). The extraction head 137 disengages from sample 810 for standard cleaning process (e.g., an N2 purge). At the same time, the system 2200 delivers a gradient to analyze the sample by LC-MS at normal flow rates and higher back pressure due to the column 1780. This approach allows the additional use of two-dimensional column chromatography (2D LC), other trap and elute approaches and ultra-high pressure/performance liquid chromatography in addition to the above described standard HPLC analysis. Compared to the system in FIGS. 21A and 21B, this set-up allows for faster extraction times.

Figure 23:
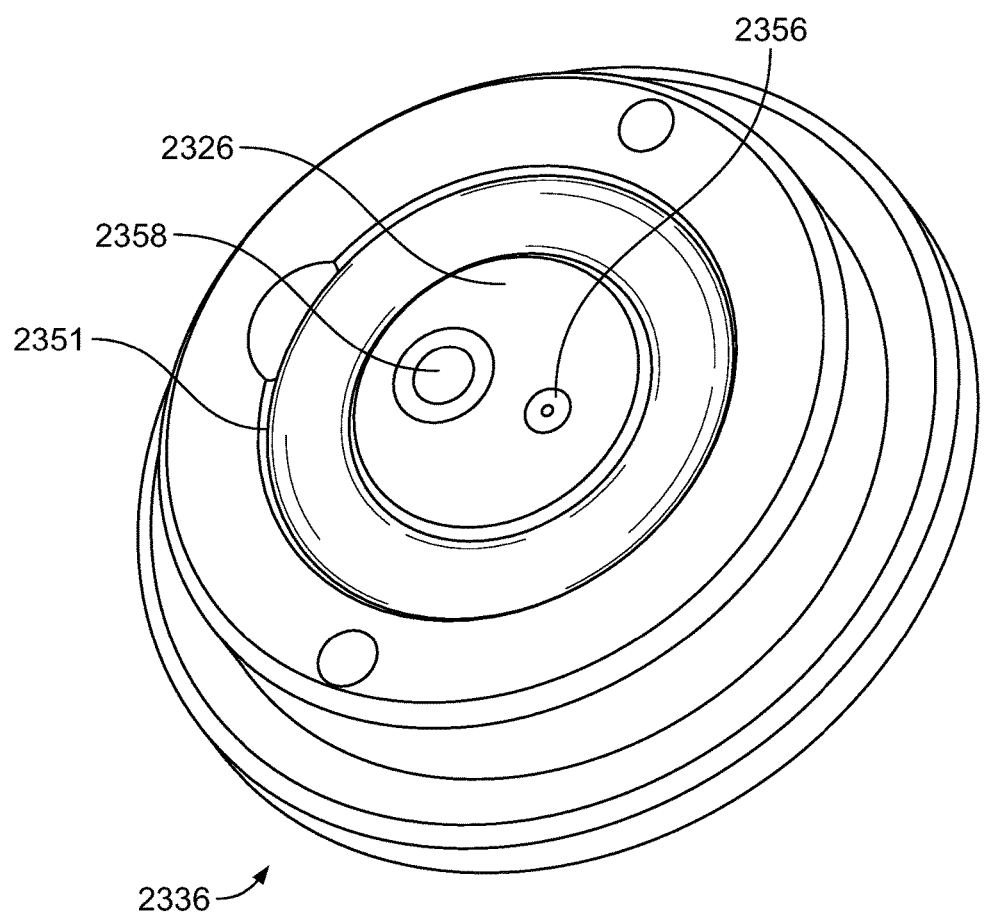
FIG. 23 is an illustration of a cavity assembly base having a sealing ring.

FIG. 23 is an illustration of a cavity assembly base having a sealing ring. FIG. 23 shows a base 2336 for use with the surface extraction interface system 100 having a cavity 2336 formed with a seal ring 2351. The cavity 2336 includes an inlet 2356 and outlet 2358, as detailed above with respect to FIG. 5. In operation, the seal ring 2351 is able to exert a similar total pressure as the metal knife-edge (see FIGS. 5 and 6), but with less damage to the surface. The seal ring 2351 configuration improves the surface extraction interface system's 100 ability to collect surface samples from soft surfaces, such as eggplant leaves. The seal ring 2351 may be made of PTFE or may be a Viton® seal ring.

A number of embodiments of the systems and methods have been described. Nevertheless, it will be understood that various modifications may be made without departing from the spirit and scope of the disclosure.

For example, the sealing cavity could be placed into a handheld device with the six port liquid assembly integrated into the MS housing and the valve switch triggered by a button on the handheld device. Because this embodiment of the device would not include the supporting surface holding up the sample to be analyzed, it would be necessary to press the device against a target by hand and the device would include, for example, an indicator how much pressure to apply when pushing against the target surface.

Accordingly, other embodiments are within the scope of the following claims.

What is claimed is:

1. A surface extraction interface system comprising:
a seal assembly comprising:
a cavity assembly defining a cavity with an inlet, an outlet, and an open side;
an actuator operable to press the cavity assembly against an opposed surface facing the open side of the cavity; and
a force gauge operable to measure a force applied by the seal assembly against the opposed surface;
wherein the actuator comprises a motor with an extendable shaft; and
wherein the force gauge comprises a spring and a sensor attached to the motor with the cavity assembly on one end of the motor shaft such that the force applied by the seal assembly against the opposed surface causes the spring to compress.

2. A surface extraction interface system comprising:
a seal assembly comprising:
a cavity assembly defining a cavity with an inlet, an outlet, and an open side;
an actuator operable to press the cavity assembly against an opposed surface facing the open side of the cavity; and
a force gauge operable to measure a force applied by the seal assembly against the opposed surface;

wherein the cavity assembly comprises a locking collar, the base detachably attached to the inlet/outlet assembly by the locking collar.

3. The system of claim 2, wherein the actuator comprises a motor with an extendable shaft.

4. The system of claim 3, wherein the motor comprises a stepper motor.

5. The system of claim 3, wherein the force gauge comprises a spring and a sensor attached to the motor with the cavity assembly on one end of the motor shaft such that the force applied by the seal assembly against the opposed surface causes the spring to compress.

6. The system of claim 1, wherein the sensor comprises a potentiometer.

7. The system of claim 1, wherein the cavity assembly comprises an inlet/outlet assembly defining at least portions of the inlet and the outlet and a base detachably attached to the inlet/outlet assembly.

8. The system of claim 2, comprising a plurality of bases defining cavities with different configurations.

9. The system of claim 1, wherein the seal assembly comprises a mechanical self-aligning washer.

10. The system of claim 1, wherein the outlet of the cavity comprises a filter assembly.

11. The system of claim 10, wherein the filter assembly comprises a flush mounted filter or an inline filter.

12. The system of claim 1, comprising a control system connected to the actuator and the force gauge, the control system responsive to input data identifying characteristics of the opposed surface to determine a force to be applied by the seal assembly against the opposed surface and to operate the actuator to achieve the force.

13. A sample analysis system comprising:
a mass spectrometer with an inlet port;
a surface extraction interface system with an outlet port and a seal assembly, the seal assembly comprising:
a cavity assembly defining a cavity with an inlet, an outlet, and an open side;
a motor with an extendable shaft, the motor operable to press the cavity assembly against an opposed surface facing the open side of the cavity; and
a force gauge operable to measure a force applied by the seal assembly against the opposed surface, wherein the force gauge comprises a spring and a potentiometer attached to the motor with the cavity assembly on one end of the motor shaft such that the force applied by the seal assembly against the opposed surface causes the spring to compress; and
a channel connecting the output port of the surface extraction interface system with the inlet port of the mass spectrometer.

14. The system of claim 13, wherein the motor comprises a stepper motor.

15. The system of claim 13, wherein the cavity assembly comprises a inlet/outlet assembly defining at least portions of the inlet and the outlet and a base detachably attached to the inlet/outlet assembly.

16. The system of claim 15, wherein the cavity assembly comprises a locking collar, the base detachably attached to the inlet/outlet assembly by the locking collar.

17. The system of claim 15, wherein the seal assembly comprising a mechanical self-aligning washer.

18. The system of claim 15, comprising a control system connected to the actuator and the force gauge, the control system responsive to input data identifying characteristics of the opposed surface to determine a force to be applied by the seal assembly against the opposed surface and to operate the actuator to achieve the force.

19. The system of claim 13, wherein the channel includes a valve assembly enabling alternating connection of the output port to a flushing system and the inlet port of the mass spectrometer.

20. The system of claim 13, wherein the channel includes a HPLC column.

21. The system of claim 13, wherein the channel includes a sample loop.

22. The system of claim 13, wherein the channel includes a first valve assembly enabling alternating connection of the output port to a flushing system and a sample loop, and a second valve assembly enabling alternating connection of an output of the sample loop to a waste line and the inlet port of the mass spectrometer.

23. The system of claim 13, wherein the a surface extraction interface system includes a rail assembly enabling translation of the cavity assembly in a first direction, and a base rail assembly enabling translation of the opposing surface in a section direction, the second direction being substantially perpendicular to the first direction.

24. The system of claim 13, wherein the cavity assembly includes a raised structure defining the cavity.

25. The system of claim 24, wherein raised structure is a knife-edge.

26. The system of claim 25, wherein raised structure is a ring seal.

27. A method of preparing a sample for analysis, the method comprising:
selecting one base from a plurality of bases defining cavities with different configurations
receiving, by a control system connected to an actuator and a force gauge, data identifying characteristics of a surface supporting the sample;
determining a pressure to be applied by a seal assembly against the surface;
sending a control signal from the control system to the actuator to operate the actuator to press a cavity assembly defining a cavity with an inlet, an outlet, and an open side against the surface facing the open side of the cavity until the pressure is achieved; and
extracting a sample from the surface.

28. The method of claim 27, wherein the force gauge comprises a spring and a sensor attached to the motor such that pressing the cavity assembly against the surface causes the spring to compress.

29. The method of claim 27, comprising assembling the cavity assembly by detachably mounting a base on an inlet/outlet assembly.

30. A method of preparing a sample for analysis, the method comprising:
receiving, by a control system connected to an actuator and a force gauge, data identifying characteristics of a surface supporting the sample;
determining a pressure to be applied by a seal assembly against the surface;
sending a control signal from the control system to the actuator to operate the actuator to press a cavity assembly defining a cavity with an inlet, an outlet, and an open side against the surface facing the open side of the cavity until the pressure is achieved; and
extracting a sample from the surface;
wherein determining the pressure comprises accessing a database of surfaces and associated pressures.

31. The method of claim 30, comprising selecting one base from a plurality of bases defining cavities with different configurations.

32. The method of claim 31, comprising forming the cavity assembly by detachably mounting the selected base on an inlet/outlet assembly defining at least portions of the inlet and the outlet.

* * * * *